United States Patent
Ding

(10) Patent No.: US 12,364,474 B2
(45) Date of Patent: Jul. 22, 2025

(54) CLOSURE DRIVE MECHANISM AND SURGICAL STAPLER

(71) Applicant: TOUCHSTONE INTERNATIONAL MEDICAL SCIENCE CO., LTD., Suzhou (CN)

(72) Inventor: Shuicheng Ding, Suzhou (CN)

(73) Assignee: TOUCHSTONE INTERNATIONAL MEDICAL SCIENCE CO., LTD., Suzhou (CN)

( * ) Notice: Subject to any disclaimer, the term of this patent is extended or adjusted under 35 U.S.C. 154(b) by 0 days.

(21) Appl. No.: 18/734,710

(22) Filed: Jun. 5, 2024

(65) Prior Publication Data

US 2024/0315691 A1  Sep. 26, 2024

Related U.S. Application Data

(63) Continuation of application No. PCT/CN2022/138719, filed on Dec. 13, 2022.

(30) Foreign Application Priority Data

| Dec. 14, 2021 | (CN) | ......................... 202111526201.1 |
| Dec. 14, 2021 | (CN) | ......................... 202111526204.5 |

(Continued)

(51) Int. Cl.
*A61B 17/072* (2006.01)
*A61B 17/068* (2006.01)

(Continued)

(52) U.S. Cl.
CPC ...... *A61B 17/068* (2013.01); *A61B 17/07207* (2013.01); *A61B 17/115* (2013.01);
(Continued)

(58) Field of Classification Search
CPC .............. A61B 17/068; A61B 17/0644; A61B 17/0686; A61B 17/072; A61B 17/07207;
(Continued)

(56) References Cited

U.S. PATENT DOCUMENTS

| 5,326,013 A | * | 7/1994 | Green | .............. | A61B 17/07207 227/176.1 |
| 5,554,169 A | * | 9/1996 | Green | .............. | A61B 17/07207 227/19 |

(Continued)

*Primary Examiner* — Scott A Smith
(74) *Attorney, Agent, or Firm* — Westbridge IP LLC

(57) ABSTRACT

A closure drive mechanism and a surgical stapler are provided, including: a linkage assembly including a first pivot portion and a second pivot portion, where the first pivot portion is configured to be pivotally connected to the instrument body, and the second pivot portion is configured to be located on a proximal side of the first pivot portion; a movable handle including a first mating portion; a closure drive assembly configured to be pivotally connected to the second pivot portion of the linkage assembly. When the linkage assembly is in a first state and the movable handle rotates in a first direction, the first mating portion drives the linkage assembly to enter a second state, the second pivot portion of the linkage assembly moves proximally and drives the closure drive assembly to move proximally, so the stapler is closed.

20 Claims, 31 Drawing Sheets

(30) Foreign Application Priority Data

| Dec. 14, 2021 | (CN) | 202111529283.5 |
|---|---|---|
| Dec. 14, 2021 | (CN) | 202111529337.8 |
| Dec. 14, 2021 | (CN) | 202123141888.5 |
| Dec. 14, 2021 | (CN) | 202123154497.7 |

(51) Int. Cl.
| | |
|---|---|
| *A61B 17/115* | (2006.01) |
| *A61B 17/00* | (2006.01) |
| *A61B 17/064* | (2006.01) |
| *A61B 17/128* | (2006.01) |
| *A61B 17/29* | (2006.01) |
| *A61B 34/00* | (2016.01) |
| *A61B 34/30* | (2016.01) |

(52) U.S. Cl.
CPC . *A61B 2017/00477* (2013.01); *A61B 17/0644* (2013.01); *A61B 17/0686* (2013.01); *A61B 17/072* (2013.01); *A61B 2017/07214* (2013.01); *A61B 17/1155* (2013.01); *A61B 17/1285* (2013.01); *A61B 17/29* (2013.01); *A61B 34/30* (2016.02); *A61B 34/71* (2016.02)

(58) Field of Classification Search
CPC ... A61B 17/115; A61B 17/1155; A61B 17/28; A61B 17/29; A61B 17/326; A61B 17/1228; A61B 17/1285; A61B 2017/00473; A61B 2017/00477; A61B 2017/07214; A61B 34/30; A61B 34/71; A61B 34/76

USPC .............. 227/19, 175.1, 175.2, 176.1, 180.1; 606/1, 139, 142, 151, 219

See application file for complete search history.

(56) References Cited

U.S. PATENT DOCUMENTS

| 5,601,573 | A | * | 2/1997 | Fogelberg | A61B 17/1227 |
| | | | | | 606/139 |
| 5,681,330 | A | * | 10/1997 | Hughett | A61B 17/1285 |
| | | | | | 606/139 |
| 5,858,018 | A | * | 1/1999 | Shipp | A61B 17/1285 |
| | | | | | 606/142 |
| 6,241,740 | B1 | * | 6/2001 | Davis | A61B 17/1227 |
| | | | | | 606/139 |
| 6,350,269 | B1 | * | 2/2002 | Shipp | A61B 17/1285 |
| | | | | | 606/151 |
| 10,835,244 | B2 | * | 11/2020 | Chen | A61B 17/0686 |
| 11,350,941 | B2 | * | 6/2022 | Chen | A61B 17/326 |
| 2008/0029576 | A1 | * | 2/2008 | Shelton | A61B 17/07207 |
| | | | | | 227/176.1 |
| 2022/0226057 | A1 | * | 7/2022 | Beckman | A61B 17/07207 |
| 2024/0315691 | A1 | * | 9/2024 | Ding | A61B 17/072 |

* cited by examiner

A3-A3

CLOSURE DRIVE MECHANISM AND SURGICAL STAPLER

CROSS-REFERENCE TO RELATED APPLICATIONS

This application is a continuation of International Application No. PCT/CN2022/138719, filed on Dec. 13, 2022, which claims priority to Chinese Patent Applications Nos. CN 202111529337.8, CN202111526204.5, CN202123141888.5, CN202123154497.7, CN202111526201.1, and CN202111529283.5, filed on Dec. 14, 2021, the entire contents of which are incorporated herein by reference.

TECHNICAL FIELD

The present disclosure relates to surgical instruments' technology, more particularly, to a closure drive mechanism and a surgical stapler.

BACKGROUND

A surgical stapler includes an instrument platform, a movable handle movably connected to the instrument platform, and a head assembly cooperated with the body. The head assembly portion includes a cartridge assembly and an anvil arranged relative to the cartridge assembly. During operation, the doctor first presses the movable handle to drive a closure drive piece proximally through a closure drive mechanism, so the cartridge assembly and the anvil are closed, and then the doctor presses the movable handle again to drive staples toward the tissue. The staples in the cartridge assembly are formed at the anvil to anastomose the tissue, and the knife moves distally to cut the tissue.

The structure of the closure drive mechanism in the prior art is relatively complex. Therefore, cost of manufacturing and maintenance is high. Furthermore, the complex structure may further cause uncertainty in closure control. During firing process of the stapler, the closure state between the cartridge assembly and the anvil may be affected as the closure drive piece may move distally, which may affect the surgical effect.

SUMMARY

To solve the problems in the prior art, the present disclosure aims to provide a closure drive mechanism and a surgical stapler, the closure drive mechanism has a simple structure and can effectively close the head assembly and maintain the closure state of the head assembly stable after being closed.

In the present disclosure, a closure drive mechanism used for a surgical stapler is provided, including: a linkage assembly including a first pivot portion and a second pivot portion, wherein the first pivot portion is configured to be pivotally connected to the instrument body, and the second pivot portion is configured to be located on a proximal side of the first pivot portion; wherein the linkage assembly has a first state and a second state; a movable handle including a first mating portion; a closure drive assembly configured to be pivotally connected to the second pivot portion of the linkage assembly; wherein, when the linkage assembly is in the first state and the movable handle rotates in a first direction, the first mating portion drives the linkage assembly to enter the second state, the second pivot portion of the linkage assembly moves proximally and drives the closure drive assembly to move proximally.

In some embodiments, the linkage assembly includes a first linkage member and a second linkage member on a proximal side of the first linkage member; wherein the first linkage member includes the first pivot portion and a third pivot portion, the second linkage member includes the second pivot portion and a fourth pivot portion, and the third pivot portion is configured to be pivotally connected to the fourth pivot portion.

In some embodiments, when the linkage assembly is in the first state and the movable handle rotates in the first direction, the first mating portion drives the first linkage member to rotate in the first direction, the second linkage member rotates in a second direction relative to the first linkage member, and an angle between the first linkage member and the second linkage member increases; wherein the second direction is opposite to the first direction.

In some embodiments, the mechanism further includes: a connecting rod, and the closure drive assembly is configured to be jacketed on the connecting rod; wherein, when the linkage assembly enters the second state from the first state, the third pivot portion and the fourth pivot portion move toward the connecting rod to drive the closure drive assembly to move toward a proximal side of the connecting rod.

In some embodiments, the mechanism further includes: a closure drive piece in the connecting rod; wherein the closure drive assembly includes a sleeve portion and a drive portion configured to be connected to the sleeve portion, the sleeve portion is configured to be jacketed on the connecting rod and connected to a proximal side of the closure drive piece, and the drive portion is configured to pivotally connected to the second pivot portion.

In some embodiments, the instrument body further includes a housing, and one of an inner surface of the housing and the drive portion of the closure drive assembly is provided with a guide slot extending in an axial direction, and the other is provided with a guide portion; wherein the guide portion is at least partially in the guide slot and movable along an extension direction of the guide slot.

In some embodiments, the closure drive assembly further includes a connecting pin, a through bore is provided on a distal side of the sleeve portion, and the connecting pin is configured to pass through both the through bore on the distal side of the sleeve portion and the proximal side of the closure drive piece to fixedly connect the sleeve portion with the closure drive piece.

In some embodiments, a fixing member is further provided on the proximal side of the connecting rod, and a closure return spring is provided between the sleeve portion and the fixing member.

In some embodiments, the mechanism further includes a groove, and the fourth pivot portion is at least partially in the groove of the third pivot portion; or, the fourth pivot portion includes a groove, and the third pivot portion is at least partially in the groove of the fourth pivot portion.

In some embodiments, the third pivot portion includes the groove, the fourth pivot portion is at least partially in the groove of the third pivot portion, and the fourth pivot portion is provided with a convex portion; wherein, when the linkage assembly is in the second state, the convex portion abuts an outer wall outside the groove to block the second linkage member from rotating in the second direction relative to the first linkage member; or, the fourth pivot portion includes the groove, the third pivot portion is at least partially in the groove of the fourth pivot portion, and the third pivot portion is provided with a convex portion;

wherein, when the linkage assembly is in the second state, the convex portion abuts the outer wall outside the groove to block the second linkage member from rotating in the second direction relative to the first linkage member.

In some embodiments, the first linkage member further includes a second mating portion, and a side surface of the second mating portion facing the movable handle is an arc-shaped surface; wherein, when the linkage assembly is in the first state and the movable handle is at an initial position of the movable handle, the second mating portion abuts the first mating portion of the movable handle.

In some embodiments, the first linkage member is a triangular rod, the first pivot portion and the third pivot portion are respectively provided at a position of a first apex and a position of a second apex of the triangular rod, and the second mating portion is provided at a position of a third apex of the triangular rod; and/or, the second linkage member is a straight rod having a first end provided with the second pivot portion and a second end provided with the fourth pivot portion.

In some embodiments, the instrument body includes a housing, the linkage assembly is in the housing, and the first pivot portion is configured to be pivotally connected to an inner surface of the housing.

In some embodiments, the mechanism further includes: a connecting rod configured to extend in an axial direction of the stapler; a closure drive piece configured to extend in the axial direction of the stapler and at least partially in the connecting rod; wherein the closure drive assembly includes: a first closure member configured to be jacketed on the connecting rod and respectively connected to a proximal side of the connecting rod and a proximal side of the closure drive piece; wherein the connecting rod is configured to drive the closure drive piece and the first closure member to rotate around a central axis of the connecting rod when the connecting rod rotates around the central axis of the connecting rod; a second closure member configured to be pivotally connected to the second pivot portion of the linkage assembly and at least partially rotatably jacketed on the first closure member; wherein the second closure member is configured to drive the closure drive piece to move proximally through the first closure member when the second closure member moves proximally.

In some embodiments, the second closure member includes a sleeve portion jacketed on the first closure member and a drive portion configured to be connected to the sleeve portion, and the first closure member is rotatable around the central axis of the connecting rod relative to the sleeve portion; wherein the drive portion is configured to be pivotally connected to the second pivot portion of the linkage assembly.

In some embodiments, the first closure member includes a shaft portion and a disc portion on a proximal side of the shaft portion; wherein a proximal side of the sleeve portion of the second closure member is provided with an annular first stepped surface, the shaft portion is at least partially in the sleeve portion, and the disc portion is on a proximal side of the first stepped surface; wherein an outer diameter of the shaft portion is smaller than an inner diameter of the first stepped surface, and the inner diameter of the first stepped surface is smaller than an outer diameter of the disc portion.

In some embodiments, a closure return spring is provided between the proximal side of the connecting rod and the shaft portion; wherein the closure return spring is configured to be compressed proximally by the shaft portion when the second closure member moves proximally.

In some embodiments, the shaft portion includes a first shaft portion and a second shaft portion, the first shaft portion is configured to be connected between the second shaft portion and the disc portion; wherein an outer diameter of the first shaft portion is smaller than that of the second shaft portion; wherein the first shaft portion is at least partially in the sleeve portion, a second stepped surface is provided between the first shaft portion and the second shaft portion, and the closure return spring is provided between the second stepped surface and the proximal side of the connecting rod.

In some embodiments, the second shaft portion is provided with a through bore, a connecting pin is configured to pass through the through bore, and the connecting pin is configured to pass through both the proximal side of the connecting rod and the proximal side of the closure drive piece.

In some embodiments, a pin groove extending in an axial direction is provided on the proximal side of the connecting rod, and the connecting pin is at least partially in the pin groove and movable along an extension direction of the pin groove.

In some embodiments, a first groove is provided on a distal side of the drive portion of the second closure member, and the second pivot portion is at least partially in the first groove; or, the second pivot portion is provided with a first groove, and a distal side of the drive portion of the second closure member is at least partially in the first groove.

In some embodiments, the mechanism further includes: an actuating member including a switch member, wherein the actuating member is movable between a first region and a second region, the second region is at a distal side of the first region; a closure drive piece having a proximal side configured to be fixedly connected to the closure drive assembly; wherein, when the linkage assembly is in the second state and the actuating member moves from the second region to the first region, the switch member forces the linkage assembly away from the actuating member, so the linkage assembly enters the first state, the third pivot portion and the fourth pivot portion move away from the actuating member, and the second pivot portion drives the closure drive piece to move distally through the closure drive assembly.

In some embodiments, the linkage assembly further includes a drive member configured to be mounted on the first linkage member or the second linkage member; wherein a first end of the drive member is convex from a side surface of the first linkage member or the second linkage member facing the actuating member; wherein, when the linkage assembly is in the second state and the actuating member moves from the second region to the first region, the switch member forces the first end of the drive member away from the actuating member.

In some embodiments, when the linkage assembly is in the second state and the actuating member moves from the first region to the second region, the first linkage member remains stationary relative to the second linkage member; wherein, when the linkage assembly is in the second state and the actuating member moves from the second region to the first region, the first linkage member is rotated relative to the second linkage member.

In some embodiments, when the linkage assembly is in the second state and the actuating member moves from the first region to the second region, the switch member drives the first end of the drive member to move distally, so the drive member doesn't block the actuating member from moving.

In some embodiments, a mounting groove is provided on a surface of the first linkage member or the second linkage member facing the actuating member, and the drive member is in the mounting groove.

In some embodiments, the mounting groove includes a first side wall, a second side wall and a bottom wall, the first side wall of the mounting groove is on a distal side of the second side wall, and a first gap is formed between the drive member and the first side wall of the mounting groove; wherein, when the linkage assembly is in the first state, the drive member abuts the second side wall of the mounting groove; wherein, when the linkage assembly is in the second state and the actuating member moves from the first region to the second region, the drive member moves toward the first side wall of the mounting groove.

In some embodiments, the linkage assembly further includes an elastic member configured to be located between the drive member and the first side wall to bias the drive member toward the second side wall; wherein the elastic member is configured to be elastically deformed by the drive member when the drive member moves toward the first side wall.

In some embodiments, the elastic member is an elastic piece, a first end of the elastic piece is configured to be connected to a side of the second side wall of the drive member facing the mounting groove, and a second end of the elastic piece is provided with a bending portion; wherein the second side wall of the mounting groove is provided with a block groove, and the bending portion of the elastic piece is in the block groove.

In some embodiments, a second end of the drive member is configured to be pivotally connected to the bottom wall of the mounting slot; at least part of an outer wall of the second end of the drive member is a first arc-shaped surface, and at least part of the bottom wall of the mounting groove is a second arc-shaped surface; wherein the first arc-shaped surface fits the second arc-shaped surface, and the first arc-shaped surface is rotatable relative to the second arc-shaped surface.

In some embodiments, the switch member is a toothed rack on a side of the actuating member facing the linkage assembly.

In some embodiments, at least one side of the first linkage member is provided with the drive member, the drive member is configured to be rotatably connected to a side wall of the first linkage member, and the switch member is a drive tooth on at least one side of the actuating member.

In some embodiments, the first linkage member is further provided with a block portion on a proximal side of the drive member, and the block portion blocks a second end of the drive member from moving proximally.

In some embodiments, the third pivot portion is configured to be pivotally connected to the fourth pivot portion through a shaft, the drive member is on the third pivot portion, and the first end of the drive member is distally rotatable around the shaft.

In some embodiments, the drive tooth includes a first side wall and a second side wall, the first side wall of the drive tooth is on a distal side of the second side wall, the first side wall of the drive tooth is a vertical surface, and the second side wall of the drive tooth is a guide surface.

In some embodiments, the mechanism further includes: a connecting rod configured to extend in an axial direction of the stapler; a closure drive piece at least partially in the connecting rod and movable in the axial direction relative to the connecting rod, wherein a first stop portion is configured to be fixedly located on a proximal side of the closure drive piece; a reset member on a proximal side of the connecting rod, wherein the reset member is at least partially in the connecting rod and movable in the axial direction relative to the connecting rod; wherein the reset member is configured to drive the closure drive piece to move distally when the reset member is driven to move distally.

In some embodiments, the closure drive mechanism further includes a second stop portion configured to be located on a proximal side of the first stop portion and fixed in the axial direction to a housing of the instrument body; wherein the reset member is configured to abut the first stop portion when the reset member is driven to move distally, and the reset member is configured to be stopped at the second stop portion when the reset member is driven to move proximally.

In some embodiments, the instrument body is provided with a mating portion for the second stop portion, and the second stop portion is configured to be rotatably connected with the mating portion.

In some embodiments, the mating portion for the second stop portion is a circumferential groove on the housing, the second stop portion is a first connecting pin configured to be movably located on the reset member, and the first connecting pin is configured to be rotatably located in the circumferential groove.

In some embodiments, the mechanism further includes an annular fixing member, the first connecting pin is configured to be fixedly connected to the fixing member, and the fixing member is rotatably in the circumferential groove.

In some embodiments, the reset member is at least partially in the fixing member, and the reset member is movable in the axial direction relative to the fixing member.

In some embodiments, the reset member includes a reset mating portion and an operating portion configured to be located on a proximal side of the reset mating portion, the operating portion is on a proximal side of the second stop portion, the second stop portion is configured to pass through the reset mating portion, and the reset mating portion is movable in the axial direction relative to the second stop portion.

In some embodiments, a side surface of the reset mating portion is provided with a sliding slot configured to extend in the axial direction, and the first connecting pin is at least partially in the sliding slot and movable along an extension direction of the sliding slot.

In some embodiments, wherein the sliding slot is not connected to a distal end and a proximal end of the reset mating portion.

In some embodiments, a first biasing member is provided between the reset mating portion and the first connecting pin, and the first biasing member is configured to bias the reset mating portion distally.

In some embodiments, a cavity is provided in the reset mating portion, and the first biasing member is a first return spring in the cavity; wherein a first end of the first return spring is configured to abut a distal end of the cavity, and a second end of the first return spring is configured to abut the first connecting pin.

In some embodiments, the first stop portion is a second connecting pin configured to pass through the proximal side of the closure drive piece, and the reset mating portion is on a proximal side of the second connecting pin; wherein, when the reset member is driven to move distally, the distal surface of the reset mating portion abuts the second connecting pin and drives the closure drive piece to move distally.

In some embodiments, the mechanism further includes a closure drive assembly, the closure drive assembly includes a sleeve portion, the sleeve portion is configured to be jacketed on the connecting rod and movable in the axial direction relative to the connecting rod; wherein the sleeve portion is configured to be fixedly connected to the proximal side of the closure drive piece through the second connecting pin; wherein a second biasing member is further provided between the sleeve portion and the second stop portion, the second biasing member is configured to bias the sleeve portion distally.

The present disclosure further provides a surgical stapler including the above closure drive mechanism.

The closure drive mechanism and the surgical stapler have the following advantages.

The present disclosure provides a closure drive mechanism used for a surgical stapler, wherein the linkage assembly is used as a transmission mechanism between the movable handle and the closure drive assembly. When the head assembly needs to be closed, the movable handle is pressed, and the movable handle can drive the closure drive assembly to move proximally through the linkage assembly, and then the closure drive assembly drives the closure drive piece to move proximally to close the head assembly. The structure is simple, and the head assembly can be effectively closed as needed. Furthermore, the closure state of the head assembly can be maintained stable through the linkage assembly.

BRIEF DESCRIPTION OF THE DRAWINGS

By reading the detailed description of non-limiting embodiments with reference to the following drawings, other features, objectives, and advantages of the present disclosure will become more apparent.

DETAILED DESCRIPTION OF THE EMBODIMENTS

Figure 1:
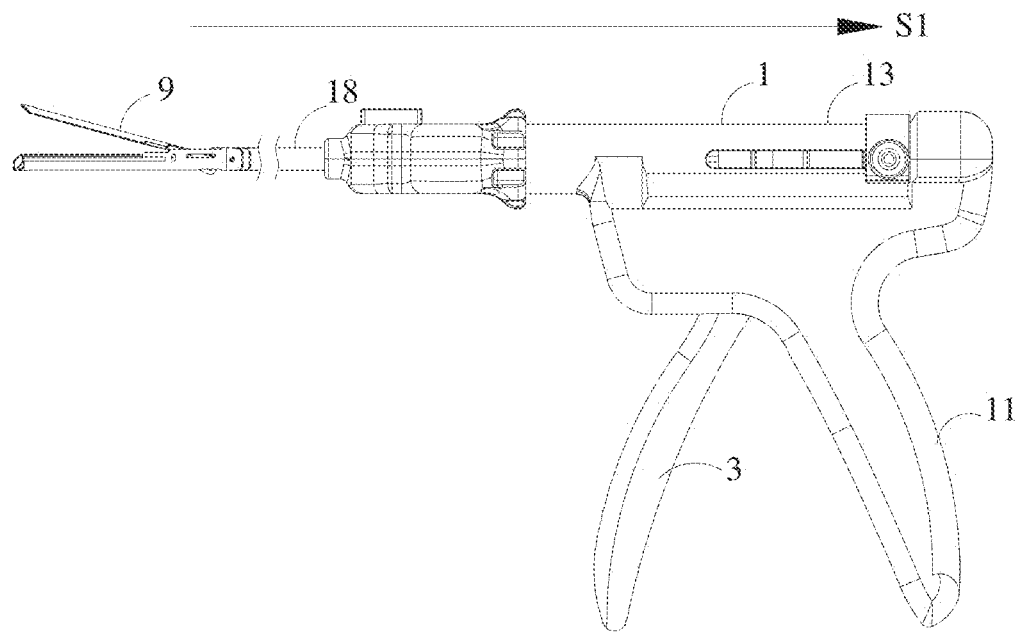
FIG. 1 is a structural schematic view of a stapler according to a first embodiment of the present disclosure.

The exemplary embodiments will be more comprehensively described by combining the drawings. However, the exemplary embodiments can be implemented in multiple forms and should not be limited to the embodiments described herein. On the contrary, providing these embodiments will make the present disclosure comprehensive and complete, and will comprehensively convey the concept of the exemplary embodiments to those skilled in the art. The same reference numbers in the drawings represent the same or similar structures, so repeated descriptions of them will be omitted.

The present disclosure provides a closure drive mechanism used for a surgical stapler and a surgical stapler including the same. The stapler further includes a head assembly and an instrument platform, and the head assembly is located on a distal side of the instrument platform. The instrument platform is provided with a closure drive piece for closing the head assembly. A distal side of the closure drive piece is connected to the head assembly. The closure drive mechanism includes: a linkage assembly including a first pivot portion and a second pivot portion, wherein the first pivot portion is pivotally connected to the instrument platform, and the second pivot portion is located on a proximal side of the first pivot portion; wherein the linkage assembly has a first state and a second state; a movable handle including a first mating portion; a closure drive assembly pivotally connected to the second pivot portion of the linkage assembly. When the linkage assembly is in the first state and the movable handle rotates in a first direction, the first mating portion drives the linkage assembly to enter the second state, the second pivot portion of the linkage assembly moves proximally, and drives the closure drive assembly to move proximally. The closure drive assembly is connected to the closure drive piece. When the closure drive assembly moves proximally, the closure drive piece is driven to move proximally, then the closure drive piece drives the head assembly to be closed.

Therefore, the linkage assembly is used as a transmission mechanism between the movable handle and the closure drive assembly. When the head assembly needs to be closed, the movable handle is pressed, and the movable handle can drive the closure drive assembly to move proximally through the linkage assembly, and then the closure drive assembly drives the closure drive piece to move proximally to close the head assembly. The structure is simple, and the head assembly can be effectively closed as needed.

The structures of the closure drive mechanisms of various specific embodiments of the present disclosure are described in detail below with reference to the accompanying drawings. It should be understood that the various specific embodiments are not intended to limit the protection scope of the present disclosure.

Figure 2:
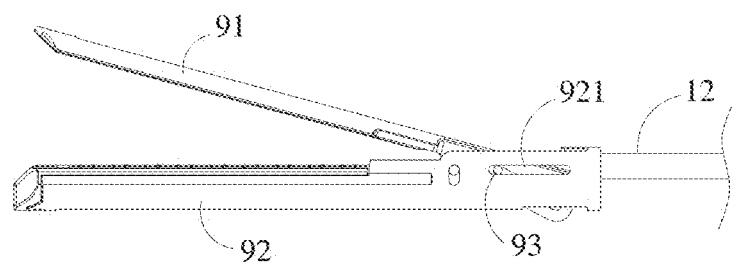
FIG. 2 is a structural schematic view of a head assembly cooperating with a closure drive piece according to the first embodiment of the present disclosure.
Figure 3:
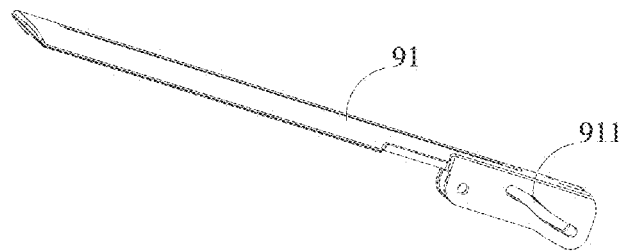
FIG. 3 is a structural schematic view of an anvil according to the first embodiment of the present disclosure.

As shown in FIGS. 1 to 12, a first embodiment of the present disclosure provides a closure drive mechanism used for a surgical stapler and the surgical stapler including the same. As shown in FIG. 1, the stapler includes a head assembly 9, an instrument platform 1 and the closure drive mechanism. The head assembly 9 is located on a distal side of the instrument platform 1. As shown in FIG. 2 and FIG. 3, the head assembly portion 9 includes an anvil 91 and a cartridge assembly 92 arranged relative to the anvil 91. The anvil 91 has a third state away from the cartridge assembly 92 and a fourth state close to the cartridge assembly 92. A proximal side of the anvil 91 is provided with an inclined first mating slot 911, and a proximal side of the cartridge assembly 92 is provided with a second mating slot 921 extending in an axial direction of the stapler. A pivot pin 93 passes through both the first mating slot 911 and the second mating slot 921. When the pivot pin 93 is located on a distal side of the second matching groove 921, the anvil 91 is in the third state, and when the pivot pin 93 moves from the distal side to a proximal side of the second matching groove 921, the anvil 91 enters the fourth state. When the anvil 91 is in the fourth state, the anvil 91 and the cartridge assembly 92 clamp tissue. The process of the anvil 91 entering the fourth state from the third state is a closure process of the head assembly 9, that is, a closure process of the stapler. The instrument platform 1 is provided with a closure drive piece 12 for closing the head assembly 9. A distal end of the closure drive piece 12 is connected to the pivot pin 93. When the closure drive piece 12 moves proximally, the pivot pin 93 can be driven to move proximally to close the head assembly 9.

In the present disclosure, the distal side and the proximal side are defined relative to the operator, the side close to the operator is the proximal side, and the side away from the operator, that is, the side close to the surgical site is the distal side. The direction along an axis of the stapler is the axial direction, that is, the direction from the distal side to the proximal side of the stapler, or from the proximal side to the distal side of the stapler. For example, in the perspective of FIG. 1, for the stapler, the distal side is the left side, and the proximal side is the right side. Direction S1 in FIG. 1 is the direction from the distal side to the proximal side of the stapler. The direction S1 or a direction opposite to the direction S1 is defined as the axial direction of the stapler. Direction S2 in FIG. 5 is defined as the longitudinal direction, that is, the height direction.

Figure 4:
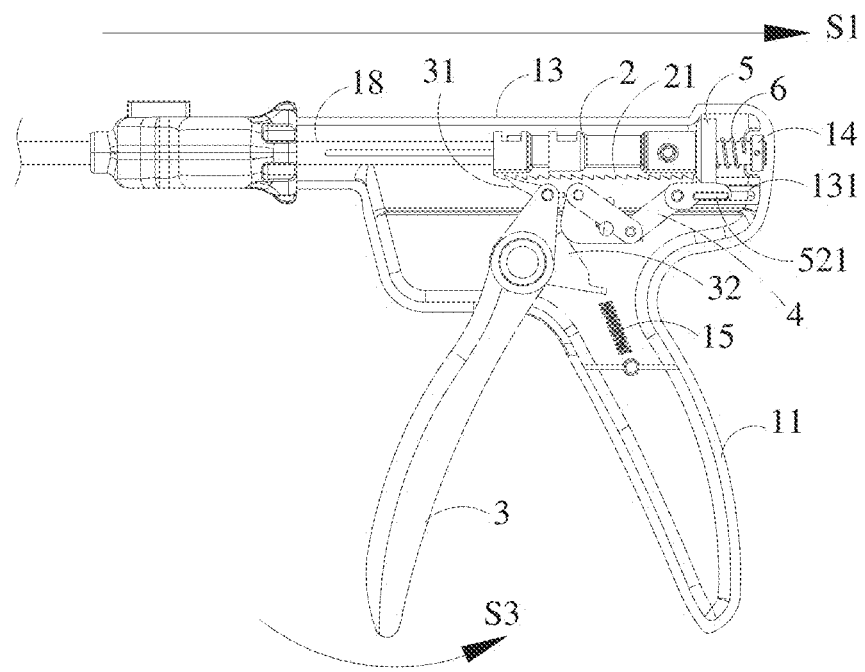
FIG. 4 is a structural schematic view of an instrument platform omitting one side of the housing according to the first embodiment of the present disclosure.

As shown in FIG. 4, the instrument platform 1 further includes a housing 13, a stationary handle 11, a connecting rod 18 extending in the axial direction and an actuating member 2 jacketed on the connecting rod 18. The closure drive piece 12 is located inside the connecting rod 18, and the closure drive piece 12 is movable in the axial direction relative to the connecting rod 18. The connecting rod 18 is a hollow tubular rod and having a distal end connected to the head assembly. A toothed rack 21 is provided on a side of the actuating member 2. The closure drive mechanism includes a linkage assembly 4, a movable handle 3 and a closure drive assembly 5. The movable handle 3 is movably connected to the instrument platform 1 and is movable relative to the stationary handle 11. FIG. 4 shows an initial position of the movable handle 3. When the movable handle 3 is not pressed, the movable handle 3 is located at the initial position away from the stationary handle 11. When the movable handle is pressed, the movable handle 3 moves toward the stationary handle 11 in a first direction (direction S3 in FIG. 6, i.e., counterclockwise direction in the perspective of FIG. 6). After the head assembly reaches the surgical site, the movable handle 3 is pressed, and the closure drive piece 12 is driven by the closure drive mechanism to move proximally, so the head assembly is closed to clamp the tissue. An end of the movable handle 3 located in the instrument platform 1 is provided with an advancement pawl 31, and the advancement pawl 31 cooperates with the toothed rack 21. After the head assembly is closed, the movable handle 3 is pressed again, the movable handle 3 moves toward the stationary handle 11, and drives the toothed rack 21 through the advancement pawl 31 to drive the actuating member 2 to move distally. The actuating member 2 drives a firing rod, so the firing rod drives a knife and a firing slide in the head assembly to move distally to fire the stapler. A return spring 15 is further provided in the instrument platform 1. When the movable handle 3 is pressed, the return spring 15 is compressed and elastically deformed. When released, the movable handle 3 is rotated away from the stationary handle 11 under the action of the deformation restoring force of the return spring 15, and then returns to the initial position of the movable handle 3.

As shown in FIGS. 5 to 8, the linkage assembly 4 includes a first pivot portion 412, a second pivot portion 422 and a second mating portion 411. The first pivot portion 412 is pivotally connected to the housing 13 of the instrument platform 1, that is, the first pivot portion 412 can only rotate relative to the instrument platform 1 but cannot move in the axial direction relative to the instrument platform 1. In the axial direction, the first pivot portion 412 is maintained at a relatively fixed position. The second pivot portion 422 is located on a proximal side of the first pivot portion 412. The linkage assembly 4 has a first state and a second state. The second pivot portion 422 is movable between a third region and a fourth region. The second region is at a proximal side of the third region. When the linkage assembly 4 is in the first state, the second pivot portion 422 is in the third region. When the linkage assembly 4 is in the second state, the second pivot portion 422 is in the fourth region. Therefore, when the linkage assembly 4 enters the second state from the first state, the second pivot portion 422 moves proximally from the third region to the fourth region. The movable handle 3 further includes a first mating portion 32 convex from a side of the movable handle 3 facing the linkage assembly 4. The closure drive assembly 5 is pivotally connected to the second pivot portion 422 of the linkage assembly 4.

Figure 5:
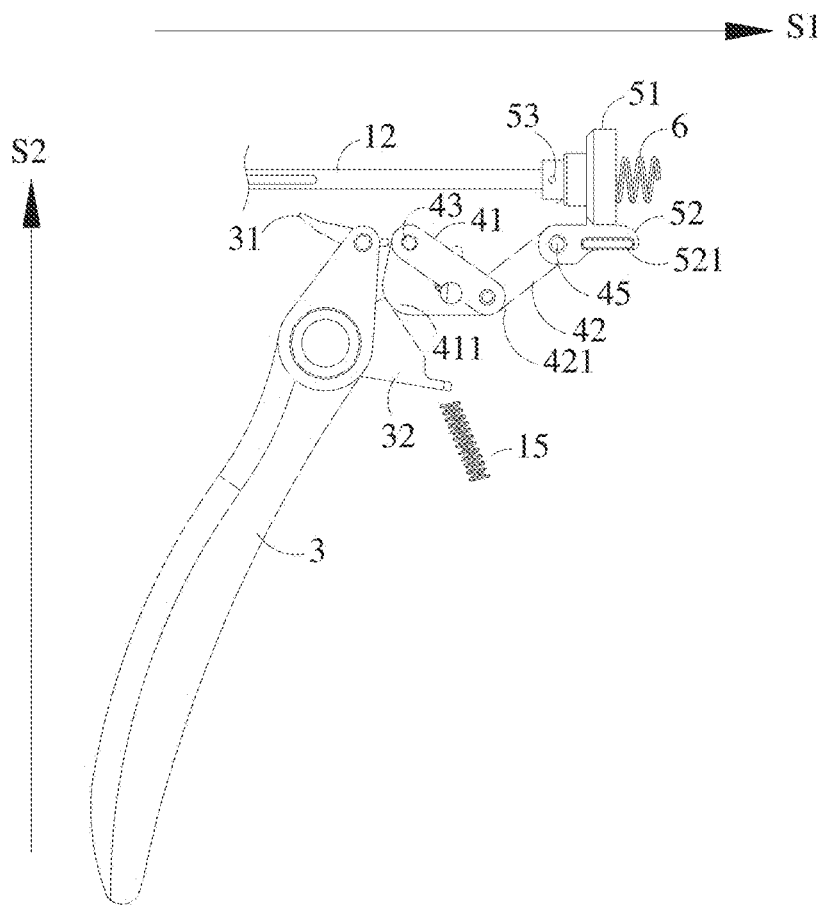
FIG. 5 is a structural schematic view of a closure drive mechanism according to the first embodiment of the present disclosure.

In an initial state, the linkage assembly 4 is in the first state, and the movable handle 3 is at its initial position shown in FIG. 5. When the linkage assembly 4 is in the first state and the movable handle 3 rotates in the direction S3, the first mating portion 32 drives the linkage assembly 4 to enter the second state through the second mating portion 411. The second pivot portion 422 of the linkage assembly 4 moves proximally, and drives the closure drive assembly 5 connected to the closure drive piece 12 to move proximally, then the closure drive piece 12 is driven by the closure drive assembly 5 to move proximally to close the head assembly 9.

The linkage assembly 4 is an assembly formed by two or more rod-shaped members connected with each other through one or more turning pairs. In this embodiment, the linkage assembly 4 is described as including two rod-shaped members. As shown in FIGS. 5 to 8, the linkage assembly 4 includes a first linkage member 41 and a second linkage member 42 located on a proximal side of the first linkage member 41. The first linkage member 41 includes the first pivot portion 412, the second mating portion 411, and a third pivot portion 413. The second mating portion 411 is located on a side of the first linkage member 41 facing the movable handle 3. The first pivot portion 412 of the first linkage member 41 is pivotally connected to the housing 13 of the instrument platform 1 through a first shaft 43. The first linkage member 41 is a triangular rod, wherein the first pivot portion 412 and the third pivot portion 413 are respectively located at a position of a first apex and a position of a second apex of the triangular rod, and the second mating portion 411 is provided at a position of a third apex the triangular rod. The structure of the triangular rod makes the cooperation between the first linkage member 41 and the movable handle 3 more stable. An outer surface of the second mating portion 411 is an arc-shaped surface. When the first mating portion 32 of the movable handle 3 drives the first linkage member 41 to rotate through the second mating portion 411, the first mating portion 32 always cooperates with the second mating portion 411 with a relatively large contact surface to avoid being jammed. In other alternative embodiments, the first linkage member 41 may be a rod in other shapes, such as a straight rod, an arc-shaped rod, a trapezoidal rod, a diamond-shaped rod, etc.

The second linkage member 42 includes the second pivot portion 422 and a fourth pivot portion 423, and the third pivot portion 413 is pivotally connected to the fourth pivot portion 423. In the embodiment, the second linkage member 42 is a straight rod, and a first end and a second end of the second linkage member 42 are respectively provided with the second pivot portion 422 and the fourth pivot portion 423. In other alternative embodiments, the second linkage member 42 may be a rod in other shapes, such as a triangular rod, an arc rod, a trapezoidal rod, a diamond rod, etc. The third pivot portion 413 is pivotally connected to the fourth pivot portion 423 through a second shaft 44, and the second pivot portion 422 is pivotally connected to the closure drive assembly 5 through a third shaft 45. In this embodiment, the third pivot portion 413 includes a groove, and the fourth pivot portion 423 is at least partially in the groove of the third pivot portion 413. In another alternative embodiment, the fourth pivot portion 423 may include a groove, and the third pivot portion 413 is at least partially in the groove of the fourth pivot portion 423.

Figure 6:
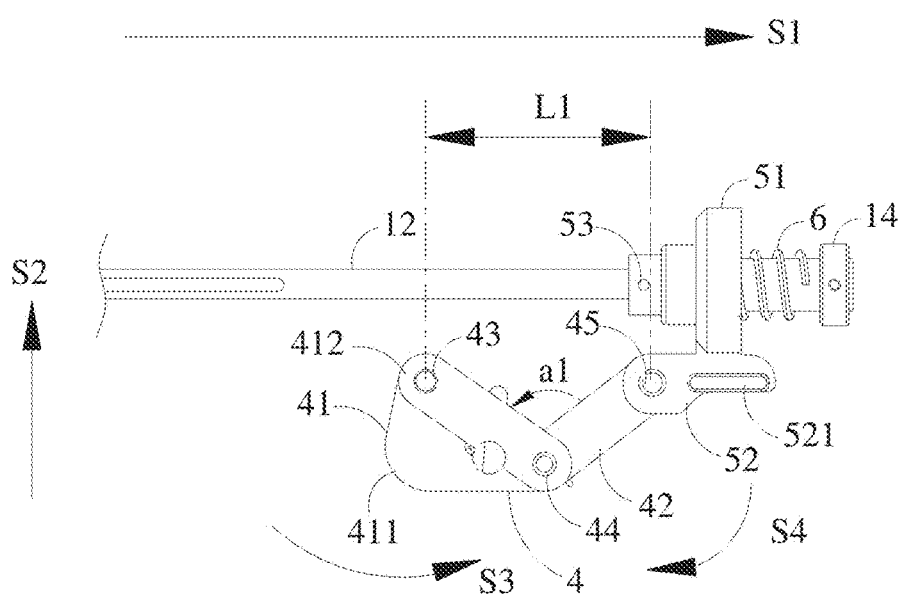
FIG. 6 is a structural schematic view of the closure drive mechanism omitting a movable handle according to the first embodiment of the present disclosure, wherein the linkage assembly is in a first state.
Figure 7:
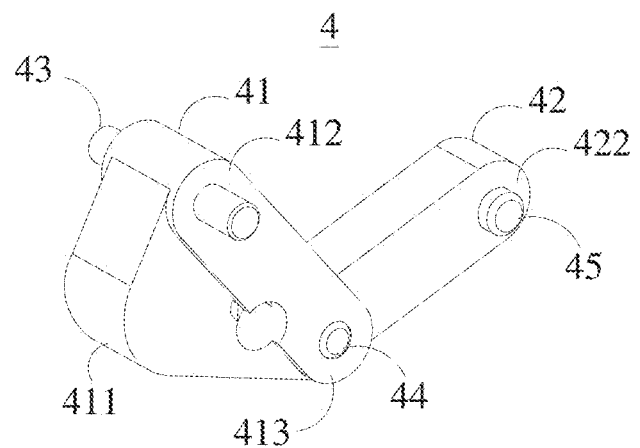
FIG. 7 is a structural schematic view of a linkage assembly in the first state according to the first embodiment of the present disclosure.
Figure 8:
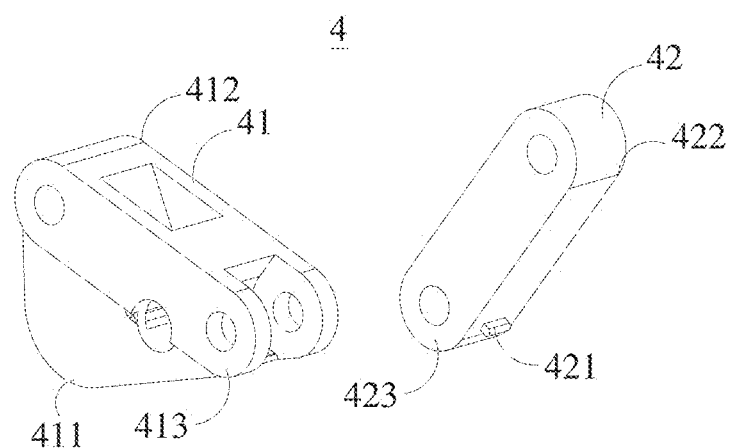
FIG. 8 is a schematic view of the first linkage member cooperating with the second linkage member according to the first embodiment of the present disclosure.

As shown in FIG. 6, when the movable handle 3 rotates in direction S3, the first linkage member 41 is driven to rotate around the first shaft 43 in the direction S3, and the second linkage member 42 rotates relative to the first linkage member 41 in the second direction, i.e., direction S4. The direction S4 is opposite to the direction S3. In the perspective of FIG. 6, the direction S4 is clockwise direction. FIG. 5 and FIG. 6 show the linkage assembly 4 cooperating with other members in the first state. The third pivot portion 413 and the fourth pivot portion 423 are located at a position relatively away from the connecting rod 18, and an angle a1 is formed between the first linkage member 41 and the second linkage member 42. The axial distance between a center of the second pivot portion 422 and a center of the first pivot portion 412 is L1, and the linkage assembly 4 is in a relatively compact state in the axial direction. At this time, an outer surface of the second mating portion 411 of the first linkage member 41 abuts the first mating portion 32 of the movable handle 3. The linkage assembly 4 is in a relatively stable state, so when the movable handle 3 is not pressed, the state of the linkage assembly 4 is maintained stable, and the closure drive assembly 5 can be well maintained at its initial position.

Figure 9:
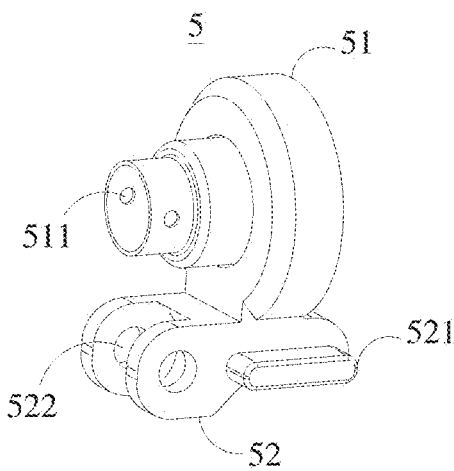
FIG. 9 is a structural schematic view of a closure drive assembly according to a first embodiment of the present disclosure.
Figure 10:
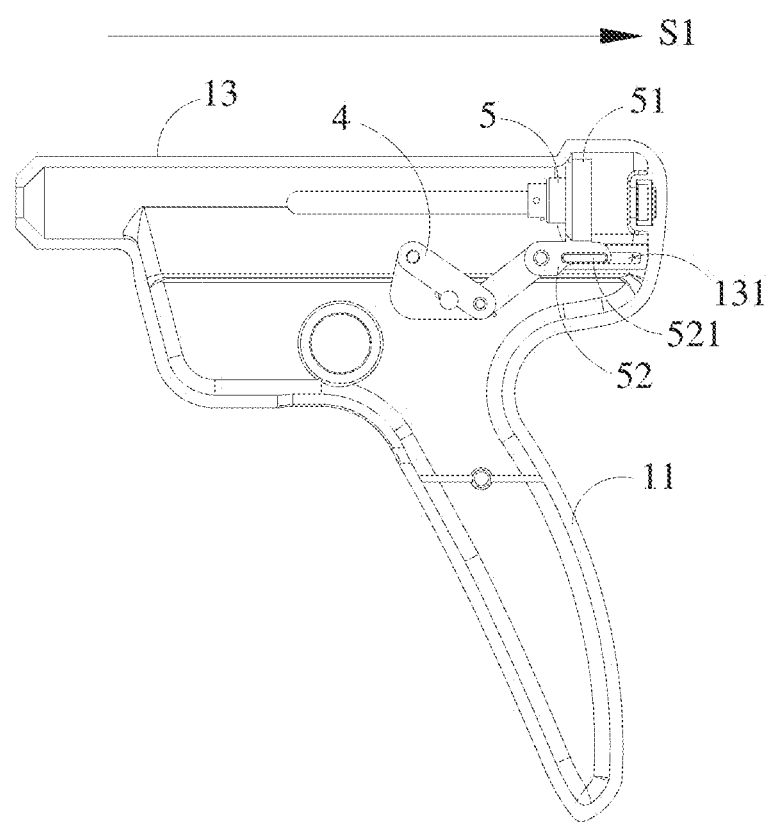
FIG. 10 is a structural schematic view of the closure drive assembly cooperating with the housing according to the first embodiment of the present disclosure.

As shown in FIGS. 6, 9 and 10, the closure drive assembly 5 includes a sleeve portion 51 and a drive portion 52 connected to sleeve portion 51. The sleeve portion 51 is jacketed on the connecting rod 18, and the drive portion 52 is pivotally connected to the second pivot portion 422. A mating hole 522 is provided on a distal side of the drive portion 52, and the third shaft 45 passes through the mating hole 522. A through bore 511 is provided on a proximal side of the sleeve portion 51, and the sleeve portion 51 is fixedly connected to a proximal side of the closure drive piece 12 through a connecting pin 53. When the drive portion 52 moves proximally, the closure drive piece 12 is driven to move proximally through the sleeve portion 51 and the connecting pin 53. A fixing member 14 is further provided on a proximal side of the connecting rod 18. The fixing member 14 is located on the proximal side of the sleeve portion 51. A closure return spring 6 is provided between the sleeve portion 51 and the fixing member 14. The closure return spring 6 can be a compression spring, for example. When the sleeve portion 51 moves proximally, the closure return spring 6 is compressed by the sleeve portion 51 to be elastically deformed. After the stapler is fired, during a process of opening the head assembly, the closure return spring 6 applies a driving force toward a distal side on the sleeve portion 51, to drive the sleeve portion 51 back to its initial position. In other alternative embodiments, the closure return spring 6 may be other kinds of springs, such as a tension spring.

As shown in FIG. 10, in this embodiment, an inner surface of the housing 13 is provided with a guide slot 131 extending in the axial direction, and the drive portion 52 of the closure drive assembly 5 is provided with a guide portion 521. The guide portion 521 is a convex strip extending in the axial direction. The guide portion 521 is at least partially in the guide slot 131 and is movable along an extension direction of the guide slot 131, so the drive portion 52 is limited to only movable in the axial direction. In another alternative embodiment, a guide portion may be provided on the inner surface of the housing 13, and the drive portion 52 of the closure drive assembly 5 may be provided with a guide slot extending in the axial direction, and the guide portion is at least partially in the guide slot and movable along an extension direction of the guide slot. The guide portion disposed on the drive portion 52 of the closure drive assembly 5 or the inner surface of the housing 13 may be a convex strip, or a convex block, a bulge, etc. The inner surfaces on two sides of the housing 13 may be respectively provided with one of guide slots or guide portions. Correspondingly, each side of the drive portion 52 may be respectively provided with one of guide portions or guide slots. In another alternative embodiment, only one side of the inner surface of the housing 13 may be provided with the guide slot or guide portion, and the side of the drive portion 52 may be provided with the guide portion or guide slot.

Figure 11:
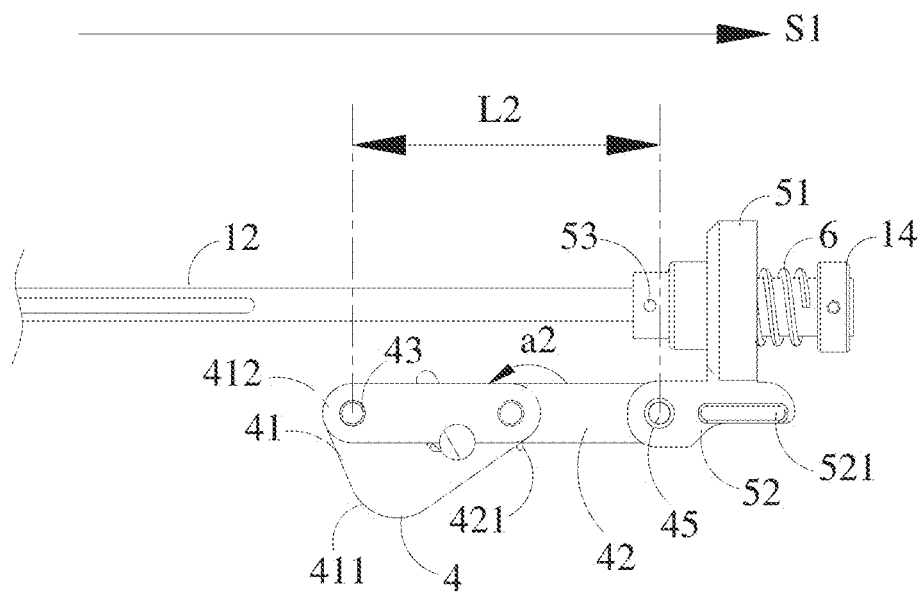
FIG. 11 is a structural schematic view of the closure drive mechanism omitting the movable handle according to the first embodiment of the present disclosure, wherein the linkage assembly is in a second state.
Figure 12:
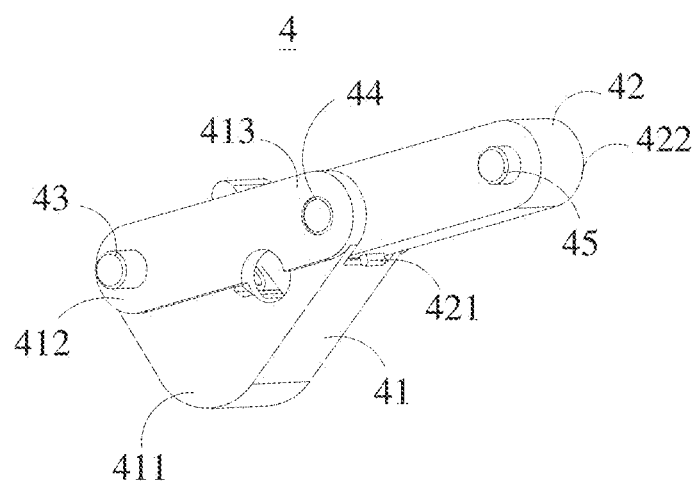
FIG. 12 is a structural schematic view of the linkage assembly in the second state according to the first embodiment of the present disclosure.

As described above, when the linkage assembly 4 is in the first state and the movable handle 3 is pressed to rotate in the direction S3, the first linkage member 41 rotates in the direction S3 around the first shaft 43, and the second linkage member 42 rotates in the direction S4 relative to the first linkage member 41, so the linkage assembly 4 enters the second state. FIGS. 11 and 12 show the structure of the linkage assembly 4 in the second state of this embodiment.

As shown in FIG. 11, during the process of the linkage assembly 4 entering the second state from the first state, the third pivot portion 413 and the fourth pivot portion 423 move toward the connecting rod 18 from the position in the first state, that is, move upward to a position relatively close to the connecting rod 18 in the perspective of FIG. 11. At this time, the linkage assembly 4 is in a relatively stable second state. The angle between the first linkage member 41 and the second linkage member 42 is a2, which is greater than the angle a1 in the first state shown in FIG. 6. In another embodiment, during the process of the linkage assembly 4 entering the second state from the first state, the angle between the first linkage rod 41 and the second linkage rod 42 gradually increases from the angle a1 in the first state to 180° and then the third pivot portion 413 and the fourth pivot portion continues to move toward the connecting rod 18 until the angle is a2. In the second state, an axial distance between the center of the first pivot portion 412 and the center of the second pivot portion 422 is L2, and the distance L2 is greater than the distance L1 in the first state shown in FIG. 6. The linkage assembly 4 is in a relatively deployed state in the axial direction. Since the first pivot portion 412 cannot be moved in the axial direction relative to the housing 13 of the instrument platform 1, the second pivot portion 422 moves proximally and drives the closure drive assembly 5 to move proximally. The sleeve portion 51 compresses the closure return spring 6 to deform, and the closure drive assembly 5 drives the closure drive piece 12 to move proximally to close the head assembly. At this time, as the second state of the linkage assembly 4 is relatively stable, even if the movable handle 3 is released and reset to its initial position under the action of the return spring 15, the linkage assembly 4 is maintained in the second state.

As shown in FIG. 12, in this embodiment, the fourth pivot portion 423 is provided with a convex portion 421. When the linkage assembly 4 is in the second state, the convex portion 421 abuts an outer wall outside the groove to prevent the second linkage member 42 from continuing to rotate in the second direction relative to the first linkage member 41, so the third pivot portion 413 and the fourth pivot portion 423 are ensured not continue to move toward the connecting rod 18, so the stability of the second state is ensured.

In another alternative embodiment, the fourth pivot portion 423 may include a groove, the third pivot portion 413 is at least partially in the groove of the fourth pivot portion 423, and the third pivot portion 413 is provided with a convex portion. Therefore, when the linkage assembly 4 is in the second state, the convex portion abuts an outer wall outside the groove to prevent the second linkage member 42 from continuing to rotate in the second direction relative to the first linkage member 41, so the stability of the second state is ensured.

Therefore, the linkage assembly 4 of the present disclosure has two stable states: the first state and the second state. When the stapler is in the initial state and the movable handle 3 is located at its initial position away from the stationary handle 11, the linkage assembly 4 is in the stable first state, so the closure drive mechanism is stable when the movable handle 3 is not pressed, and the closure drive piece 12 will not move in the axial direction. When the stapler needs to be closed, the movable handle 3 is pressed to rotate toward the stationary handle 11, so the linkage assembly 4 is driven to enter the second state and then maintained in the stable second state. At this time, the closure drive piece 12 is moved proximally to close the head assembly. In this state, when the movable handle 3 is pressed to continue to rotate, as the advanced pawl 31 of the firing handle 3 cooperates with the toothed rack 21, the firing rod inside the instrument platform 1 is moved by the toothed rack to drive the head assembly to fire the stapler. During the firing process of the stapler, the linkage assembly 4 is always maintained stably in the second state, so the closure drive piece 12 is ensured not to move distally, and the surgical effect is improved.

FIGS. 13 to 27 show the structure of the closure drive mechanism of the second embodiment of the present disclosure. During surgery, the doctor needs the head assembly to be flexibly rotatable relative to the instrument platform to meet the requirements in complex surgical situations. The second embodiment provides a simple and effective solution. When the doctor operates the instrument platform, the head assembly can flexibly rotate in a range of 360°, so the stapler is convenient to operate for the doctor. In the second embodiment, when the connecting rod rotates around its central axis, the connecting rod drives the head assembly to rotate synchronously, so the head assembly is rotatable around the central axis of the connecting rod.

In this second embodiment, the closure drive assembly includes a first closure member and a second closure member, the first closure member surrounds outside the connecting rod, the first closure member is respectively connected to a proximal side of the connecting rod and a proximal side of the closure drive piece. The second closure member is at least partially jacketed on the first closure member. The first closure member is rotatable around the central axis of the connecting rod relative to the second closure member.

Wherein, the first closure member is relatively fixed to the closure drive piece in the axial direction. When the second closure member moves proximally, the closure drive piece is driven by the first closure member to move proximally to close the head assembly. The first closure member, the closure drive piece and the connecting rod are relatively fixed in a circumferential direction of the connecting rod. When the connecting rod rotates around the central axis of the connecting rod, the closure drive piece and the first closure member are driven to rotate around the central axis of the connecting rod. Therefore, when the head assembly is driven to rotate by the connecting rod, the closure drive piece and the first closure member rotate synchronously, while the second closure member does not rotate, so the closure function of the closure drive mechanism is not affected. Therefore, when the connecting rod rotates, the closure drive piece and the first closure member are driven to rotate together. The rotation of the connecting rod drives the head assembly to rotate. Furthermore, as the first closure member is rotatable relative to the second closure member, when the first closure member rotates, the second closure member is prevented from rotating, so as not to affect the closure function of the closure drive mechanism. The head assembly is rotatable in a range of 360°.

Figure 13:
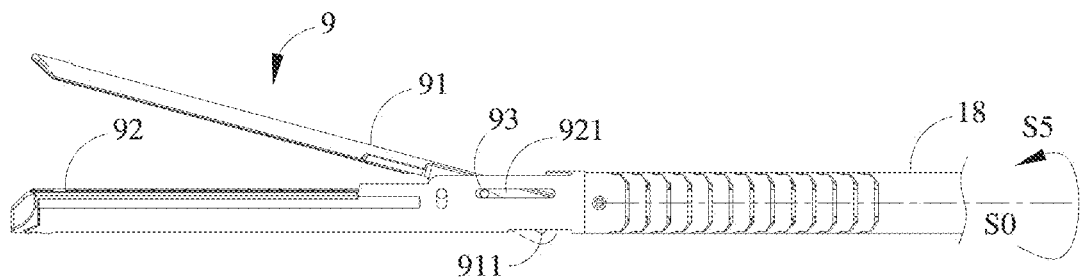
FIG. 13 is a schematic view of a head assembly cooperating with a connecting rod according to a second embodiment of the present disclosure.
Figure 14:
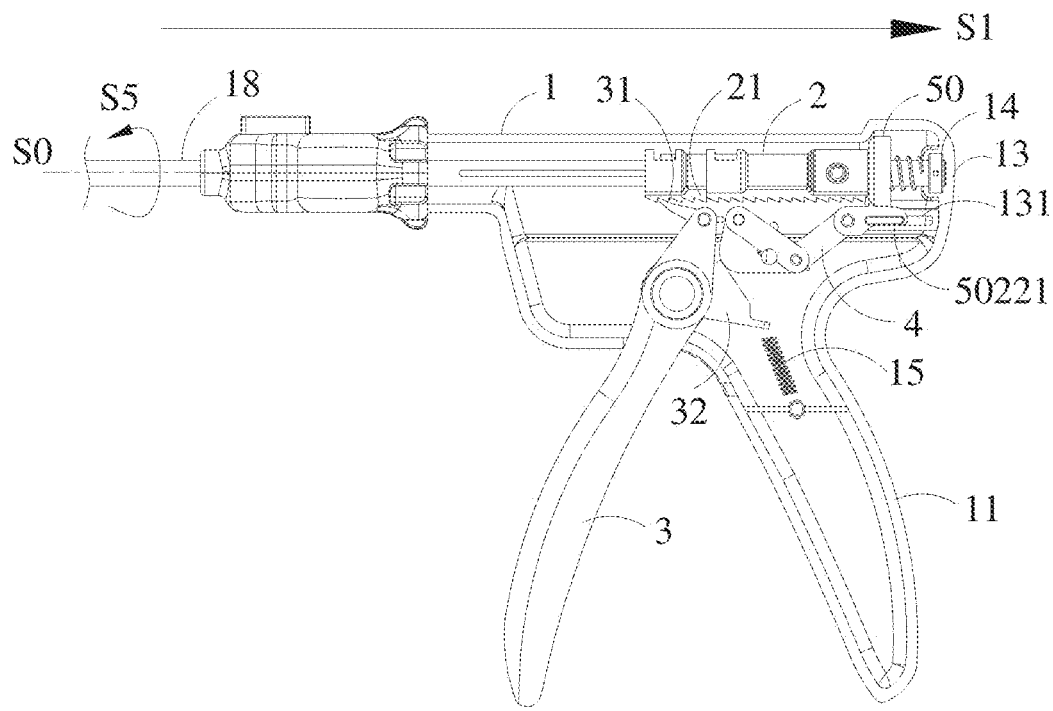
FIG. 14 is a structural schematic view of an instrument platform omitting one side of a housing according to the second embodiment of the present disclosure.

As shown in FIGS. 13 to 27, the second embodiment provides a closure drive mechanism used for a surgical stapler and a surgical stapler including the same. The structure of the closure drive assembly 50 of the second embodiment is different from that of the closure drive assembly 5 of the first embodiment. As shown in FIGS. 13 and 14, the stapler includes a head assembly 9, an instrument platform 1 and a closure drive mechanism, wherein the head assembly 9 is located on a distal side of the instrument platform. The closure drive mechanism includes a connecting rod 18, a closure drive piece 12 and a closure drive assembly 5. As shown in FIG. 13, the head assembly portion 9 includes an anvil 91 and a cartridge assembly 92 arranged relative to the anvil 91. The anvil 91 has a third state away from the cartridge assembly 92 and a fourth state close to the cartridge assembly 92. The structure and principle of closing the head assembly 9 by the closure drive piece 12 are the same as those of the first embodiment and are not described in detail here.

As shown in FIGS. 13 and 14, a connecting rod 18 extends in the axial direction of the stapler, and the connecting rod 18 is at least partially in a housing 13 of the instrument platform 1. A distal side of the connecting rod 18 is connected to the head assembly 9. When the connecting rod 18 rotates in direction S5 around a central axis S0 of the connecting rod 18, the head assembly is driven to rotate synchronously by the connecting rod 18, so the head assembly 9 is rotatable in the direction S5 around the central axis S0, and even in a range of 360° relative to the central axis S0 of the connecting rod 18.

Figure 15:
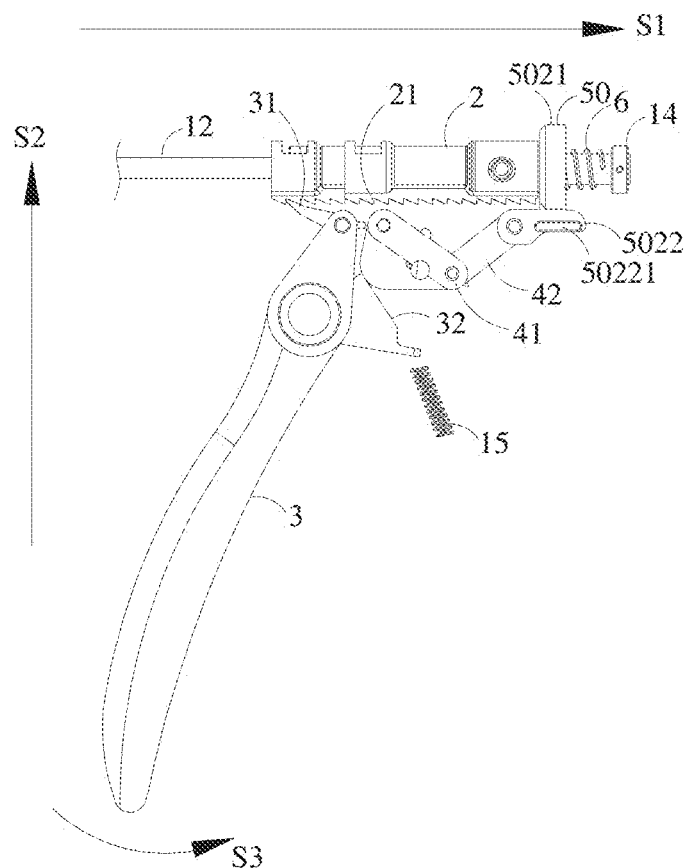
FIG. 15 is a structural schematic view of a closure drive mechanism according to the second embodiment of the present disclosure.
Figure 16:
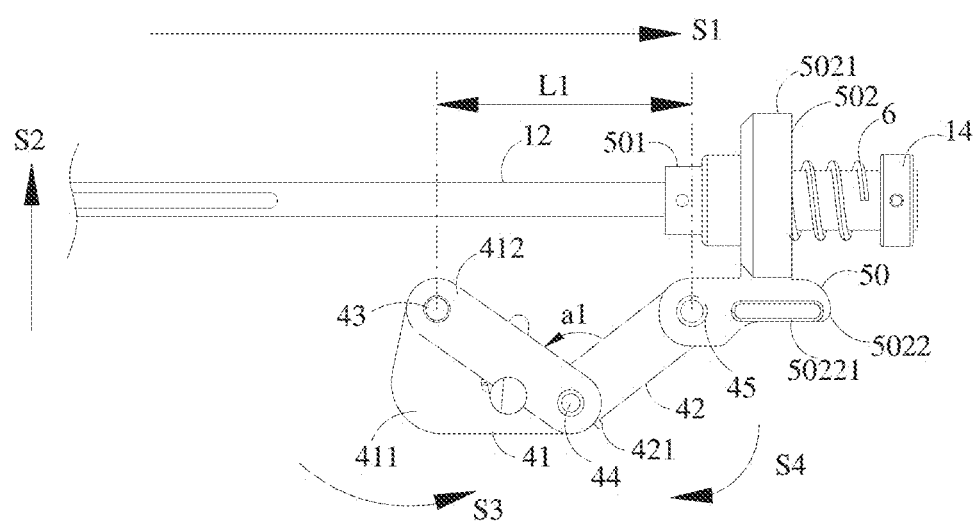
FIG. 16 is a structural schematic view of the closure drive mechanism in a first state according to the second embodiment of the present disclosure.
Figure 17:
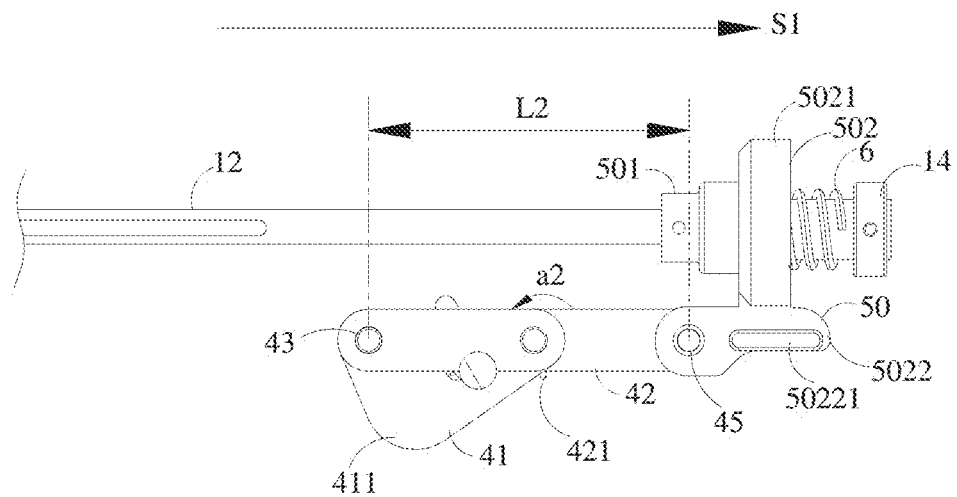
FIG. 17 is a structural schematic view of the closure drive mechanism in a second state according to the second embodiment of the present disclosure.

As shown in FIGS. 15 to 17, the closure drive piece 12 extends in the axial direction of the stapler and is at least partially in the connecting rod 18. The closure drive assembly 50 includes a first closure member 501 and a second closure member 502. The first closure member 501 surrounds outside the connecting rod 18, and the first closure member 501 is respectively connected to a proximal side of the connecting rod 18 and a proximal side of the closure drive piece 12. The second closure member 502 is at least partially jacketed on the first closure member 501, and the first closure member 501 is rotatable around the central axis of the connecting rod 18 relative to the second closure member 502.

The first closure member 501 is relatively fixed to the closure drive piece 12 in the axial direction of the stapler. When the second closure member 502 moves proximally, the first closure member 501 drives the closure drive piece 12 to move proximally to close the head assembly. The first closure member 501, the closure drive piece 12 and the connecting rod 18 are relatively fixed in the circumferential direction of the connecting rod 18. When the connecting rod 18 rotates around the central axis of the connecting rod 18, the closure drive piece 12 and the first closure member 501 are driven to rotate around the central axis of the connecting rod 18. Therefore, when the head assembly is driven to rotate by the connecting rod 18, the closure drive piece 12 and the first closure member 501 rotate synchronously, while the second closure member 502 does not rotate, and the closure function of the closure drive mechanism will not be affected.

As shown in FIGS. 15 to 17, in this embodiment, the closure drive mechanism further includes a transmission assembly and a movable handle 3. The transmission assembly is used for transmitting the force between the movable handle 3 and the second closure member 502. In this embodiment, the transmission assembly is a linkage assembly 4 including two or more rod-shaped members connected to each other by a turning pair. As shown in FIG. 15, the instrument platform 1 includes a housing 13, a stationary handle 11, and an actuating member 2 jacketed on a connecting rod 18, and the closure drive piece 12 is in the connecting rod 18. A toothed rack 21 is provided on one side of the actuating member 2. The movable handle 3 is movably connected to the instrument platform 1 and is movable relative to the stationary handle 11. FIG. 15 shows the initial position of the movable handle 33. When the movable handle 33 is pressed, the movable handle 3 moves in direction S3 toward the stationary handle 11. The movable handle 3 drives the closure drive assembly 50 to move proximally through the linkage assembly 3, so the head assembly is closed to clamp the tissue. One end of the movable handle 3 that enters the instrument platform 1 is provided with an advancement pawl 31, and the advancement pawl 31 is cooperated with the toothed rack 21. After the head assembly is closed, the movable handle 3 is pressed again, the toothed rack 21 is driven by the advancement pawl 31 to drive the actuating member 2 to move distally, so the firing rod located in the instrument platform 1 is moved to drive the knife and the firing slide in the head assembly to fire the stapler. A return spring 15 is provided in the instrument platform 1 and has the same function as that of the first embodiment. As shown in FIGS. 15 to 17, the linkage assembly 4 includes a first pivot portion 412 pivotally connected to the instrument platform 1 and a second pivot portion 422. The second pivot portion 422 is located on a proximal side of the first pivot portion 412, and the second pivot portion 422 is pivotally connected to the second closure member 502. The linkage assembly 4 has a first state shown in FIG. 16 and a second state shown in FIG. 17, and the movable handle 3 includes a first mating portion 32. In this embodiment, the linkage assembly 4 includes a first linkage member 41 and a second linkage member 42 on a proximal side of the first linkage member 41. The first linkage member 41 includes the first pivot portion 412, a third pivot portion 413 and a mating portion, the second linkage member 42 includes the second pivot portion 422 and a fourth pivot portion 423. The third pivot portion 413 is pivotally connected to the fourth pivot portion 423. When the linkage assembly 4 is in the first state, an axial distance between a center of the first pivot portion 412 and a center of the second pivot portion 422 is L1. At this time, the third pivot portion 413 and the fourth pivot portion 423 are located at a position relatively away from the connecting rod 18, and an angle a1 is formed between the first linkage member 41 and the second linkage member 42. An outer surface of the second mating portion 411 of the first linkage member 41 abuts the first mating portion 32 of the movable handle 3. The linkage assembly 4 is in a relatively stable state, so the state of the linkage assembly 4 will not change when the movable handle 3 is not pressed, and the closure drive assembly 50 can be well maintained in its initial position. The linkage assembly 4 is in a relatively compact state in the axial direction. A fixing member 14 is located on the proximal side of the connecting rod 18, and a closure return spring 6 is disposed between the closure drive mechanism and the fixing member 14. The closure return spring 6 may be, for example, a compression spring.

When the linkage assembly 4 is in the first state shown in FIG. 16 and the movable handle 3 rotates in the direction S3, the first linkage member 41 rotates in the first direction (direction S3) around the first shaft 43, and the second linkage member 42 rotates in the second direction (direction S4) relative to the first linkage member 41, so the linkage assembly 4 enters the second state shown in FIG. 17. The second direction is opposite to the first direction. In the perspective of FIG. 16, the first direction (direction S3) is counterclockwise direction, and the second direction (direction S4) is clockwise direction. As shown in FIG. 17, the third pivot portion 413 and the fourth pivot portion 423 move toward the connecting rod 18 compared to the position in the first state, that is, move upward to a position relatively close to the connecting rod 18 in the perspective of FIG. 17. At this time, the linkage assembly 4 is in a relatively stable second state. The angle between the first linkage member 41 and the second linkage member 42 is a2, which is greater than the angle a1 in the first state shown in FIG. 16. The distance between the center of the first pivot portion 412 and the center of the second pivot portion 422 is L2, and the distance L2 is greater than the distance L1 in the first state shown in FIG. 16. The linkage assembly 4 is in a relatively deployed state in the axial direction. As the first pivot portion 412 cannot be moved in the axial direction relative to the housing 13 of the instrument platform 1, the second pivot portion 422 moves proximally and drives the second closure member 502 of the closure drive assembly 50 to move proximally. The closure drive assembly 50 compresses the closure return spring 6 to deform, and the second closure member 502 drives the closure drive piece 12 to move proximally through the first closure member 501 to close the head assembly.

Figure 19:
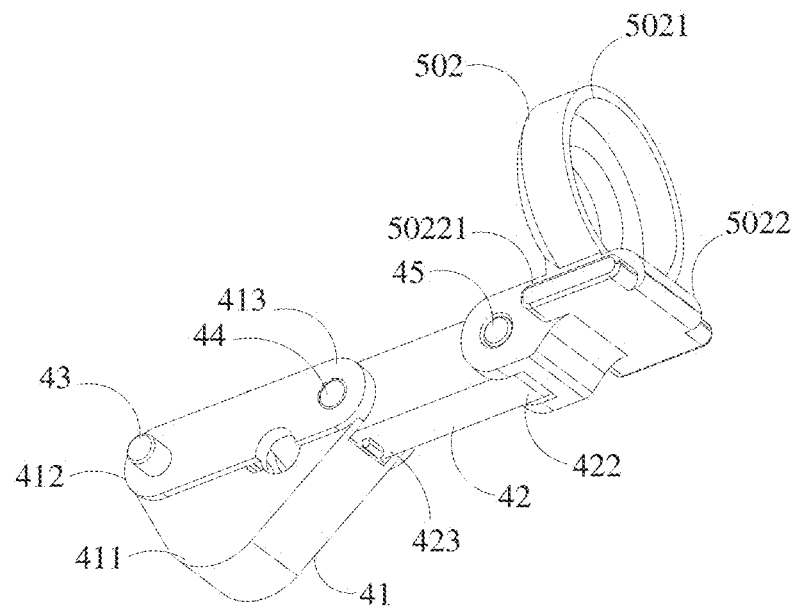
FIG. 19 is a structural schematic view of the linkage assembly in the second state cooperating with the second closure member according to the second embodiment of the present disclosure.
Figure 20:
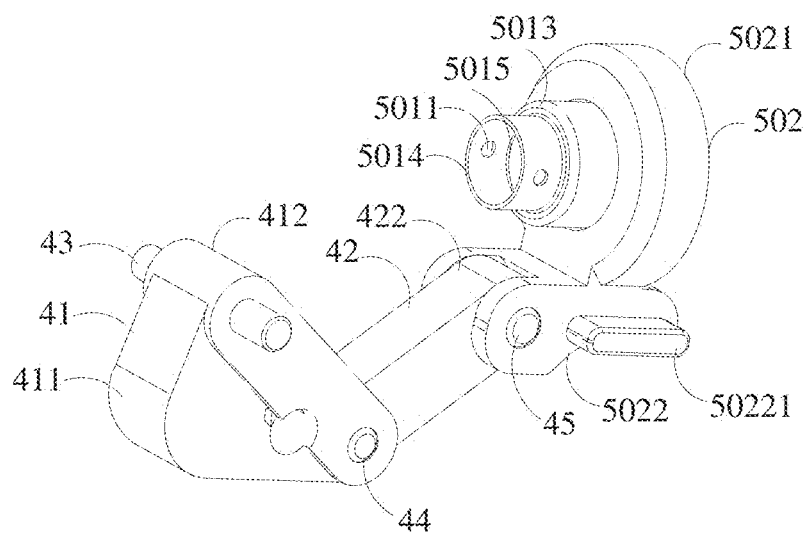
FIG. 20 is a structural schematic view of the linkage assembly cooperating with a closure drive assembly according to the second embodiment of the present disclosure.

FIG. 19 and FIG. 20 respectively show the linkage assembly 4 cooperating with the second closure member 502 in the first state and the second state. As shown in FIGS. 19 and 20, the first pivot portion 412 of the first linkage member 41 is pivotally connected to the housing 13 of the instrument platform 1 through a first shaft 43. The third pivot portion 413 is pivotally connected to the fourth pivot portion 423 through a second shaft 44, and the second pivot portion 422 is pivotally connected to the first mating portion 32 through a third shaft 45. The specific shapes and structures of the first linkage member 41 and the second linkage member 42 are the same as those in the first embodiment and are not described in detail herein. Therefore, the linkage assembly 4 of the present disclosure has two stable states: the first state and the second state. When the stapler is in the initial state and the movable handle 3 is located at its initial position away from the stationary handle 11, the linkage assembly 4 is in a stable first state, so the closure drive mechanism is maintained stable when the movable handle 3 is not pressed, and the closure drive piece 12 will not move in the axial direction. When the stapler needs to be closed, the movable handle 3 is pressed to rotate toward the stationary handle 11, the linkage assembly 4 is driven to enter the second state and then maintained in the stable second state. At this time, the closure drive piece 12 is moved proximally to close the head assembly. As the second state of the linkage assembly 4 is relatively stable, even if the movable handle 3 is released and reset to its initial position under the action of the return spring 15, the linkage assembly 4 can be maintained in the second state. At this time, when the movable handle 3 is pressed again, the advancement pawl 31 of the movable handle 3 drives the toothed rack 21 of the actuating member 2 to move, the firing rod inside the instrument platform 1 is moved to drive the head assembly to fire the stapler. During the firing process of the stapler, the linkage assembly 4 can always be stably maintained in the second state, so the closure drive piece 12 is ensured not to move distally, so the surgical effect is improved.

Figure 21:
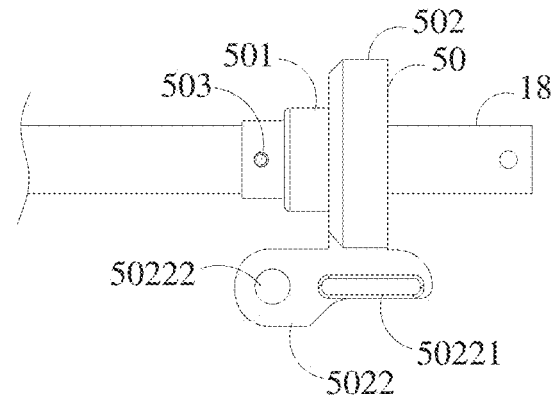
FIG. 21 is a front view of the linkage assembly cooperating with the closure drive assembly according to the second embodiment of the present disclosure.

As shown in FIGS. 20 and 21, in this embodiment, the second closure member 502 includes a sleeve portion 5021 and a drive portion 5022 connected to the sleeve portion 5021. The sleeve portion 5021 is jacketed on the first closure member 501, and the first closure member 501 is rotatable around the central axis of the connecting rod 18 relative to the sleeve portion 5021. A mating hole 50222 cooperated with the third shaft 45 is provided on a distal side of the drive portion 5022. A first groove is disposed on a distal side of the drive portion 5022 of the second closure member 502, an inner wall of the first groove is provided with the mating hole 50222, and the second pivot portion 422 is at least partially in the first groove. In another alternative embodiment, the second pivot portion 422 may be provided with a first groove, and a distal side of the drive portion 5022 of the second closure member 502 is at least partially in the first groove.

As shown in FIG. 14, an inner surface of the housing 13 is provided with a guide slot 131 extending in the axial direction, and the drive portion 5022 of the closure drive assembly 50 is provided with a guide portion 50221. As shown in FIGS. 20 and 21, the guide portion 50221 is a convex strip extending in the axial direction, and the guide portion 50221 is at least partially in the guide slot 131 and movable along an extension direction of the guide slot 131, so the drive portion 5022 is limited to be only movable in the axial direction. The drive portion 5022 cannot rotate relative to the housing 13, and the rotation of the first closure member 501 cannot rotate the drive portion 5022, so a relatively stable cooperation between the drive portion 5022 and the linkage assembly 4 is maintained. In another alternative embodiment, a guide portion may be provided on the inner surface of the housing 13, and the drive portion 5022 of the closure drive assembly 50 may be provided with a guide slot extending in the axial direction, and the guide portion is at least partially in the guide slot and movable along the extension direction of the guide slot. The guide portion on the drive portion 5022 of the closure drive assembly 50 or the inner surface of the housing 13 may be a convex strip, or a convex block, a bulge, etc. The inner surfaces of two sides of the housing 13 may be respectively provided with one of guide slots or guide portions. Correspondingly, each side of the drive portion 5022 may be provided with one of guide portions or guide slots. In another alternative embodiment, only one side of the inner surface of the housing 13 may be provided with the guide slot or the guide portion, and the side of the drive portion 5022 may be provided with the guide portion or the guide slot.

Figure 22:
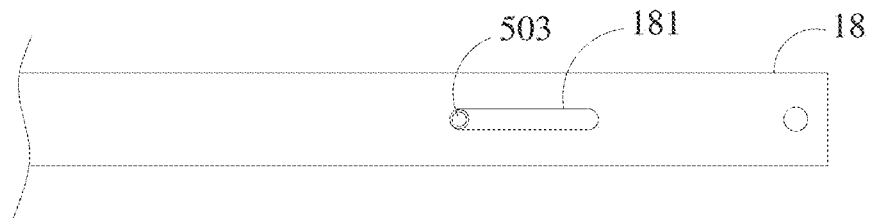
FIG. 22 is a schematic view of a connecting rod cooperating with a connecting pin according to the second embodiment of the present disclosure.
Figure 23:
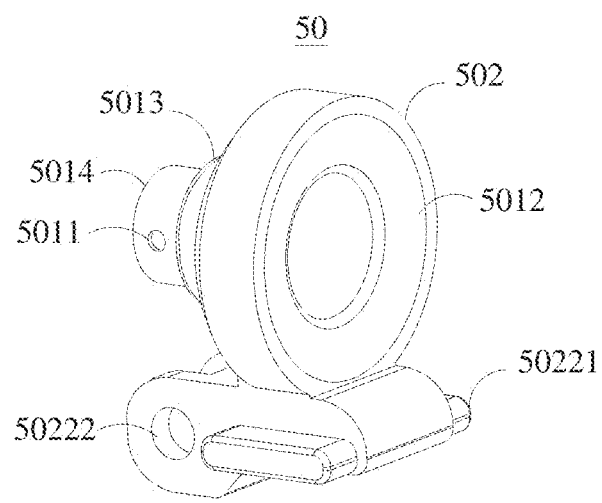
FIG. 23 is a structural schematic view of the closure drive assembly according to the second embodiment of the present disclosure.
Figure 24:
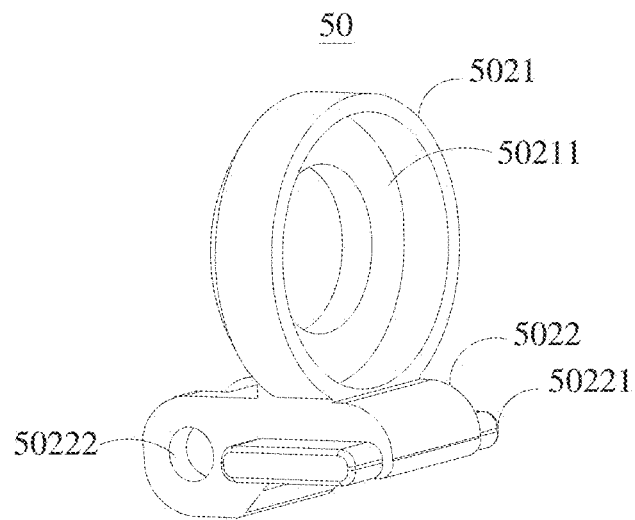
FIG. 24 is a structural schematic view of the second closure member according to the second embodiment of the present disclosure.

As shown in FIGS. 21 and 22, the second shaft portion 5014 is provided with a through bore 5011, a connecting pin 503 passes through the through bore 5011, and the connecting pin 503 passes through both the proximal side of the connecting rod 18 and the proximal side of the closure drive piece 12. The connecting pin 503 cooperates with the closure drive piece 12 in the following manner: a hole sized to fit an outer diameter of the connecting pin 503 is provided on the proximal side of the closure drive piece 12, and the connecting pin 503 passes through the hole on the proximal side of the closure drive piece 12. When the first closure member 501 moves proximally, the closure drive piece 12 is moved proximally through the connecting pin 503. The connection pin 503 cooperates with the connection rod 18 in the following manner: a pin groove 181 extending in the axial direction is provided on the proximal side of the connection rod 18, and the connection pin 503 is at least partially in the pin groove 181 and movable along an extension direction of the pin groove 181. Therefore, when the first closure member 501 moves proximally, the connecting pin 503 moves in the axial direction in the pin groove 181 without driving the connecting rod 18 to move in the axial direction. When the linkage assembly 4 is in the first state, the connecting pin 503 is on a distal side of the pin groove 181. When the linkage assembly 4 enters the second state from the first state, the connecting pin 503 is driven to move proximally through the second closure member 502 and the first closure member 501 in sequence, so the connecting pin 503 moves to the proximal side of the pin groove 181. At the same time, the first closure member 501, the closure drive piece 12 and the connecting rod 18 form a circumferentially fixed connection through the pin groove 181, that is, when the connecting rod 18 drives the head assembly to rotate around the central axis of the connecting rod 18, the closure drive piece 12 and the first closure member 501 are simultaneously driven to rotate around the central axis of the connecting rod 18 through the connecting pin 503. At this time, the second closure member 502 does not rotate and maintains a stable cooperation with the linkage assembly 4.

Figure 18:
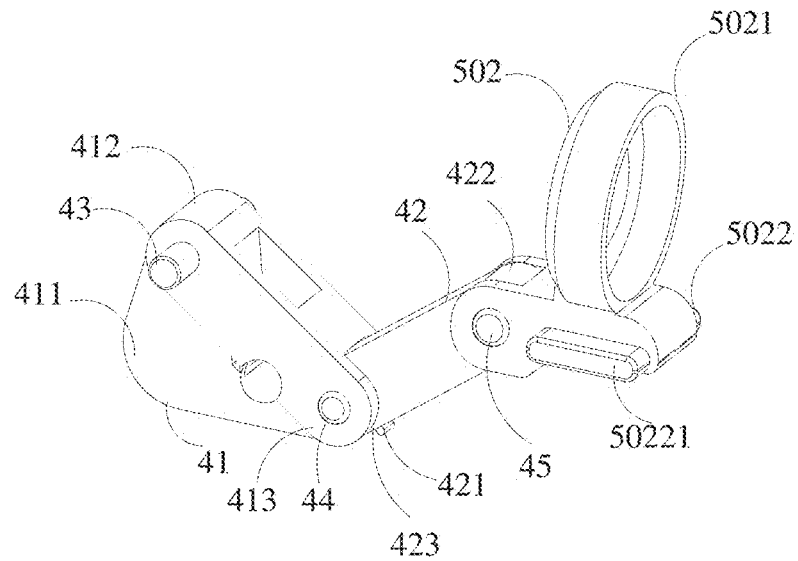
FIG. 18 is a structural schematic view of a linkage assembly in the first state cooperating with a second closure member according to the second embodiment of the present disclosure.
Figure 25:
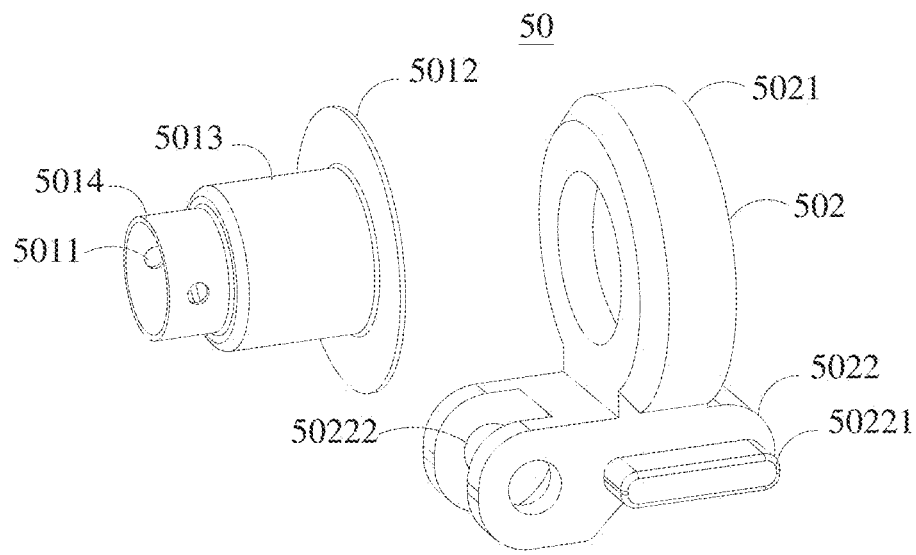
FIG. 25 is a schematic view of the closure drive assembly according to the second embodiment of the present disclosure.
Figure 26:
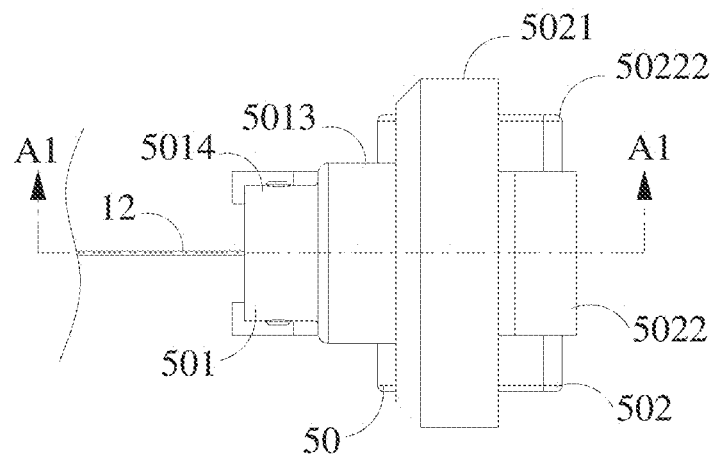
FIG. 26 is a structural schematic view of the closure drive assembly cooperating with the closure drive piece according to the second embodiment of the present disclosure.
Figure 27:
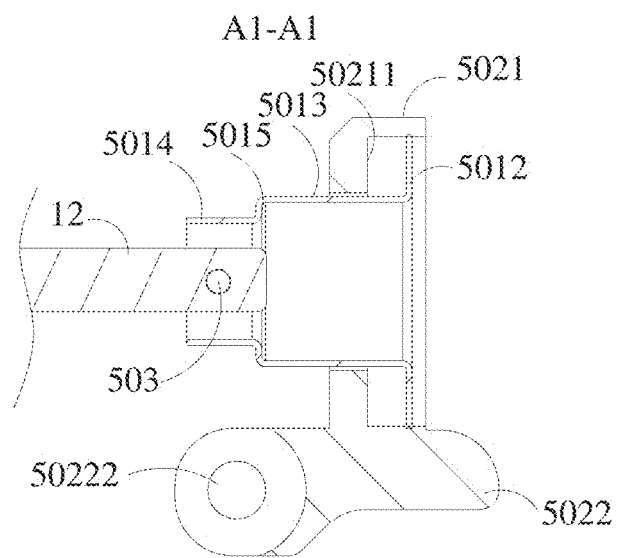
FIG. 27 is a cross-sectional view taken in direction A1-A1 in FIG. 26.

As shown in FIG. 25, the first closure member 501 includes a shaft portion and a disc portion 5012, the shaft portion includes a first shaft portion 5013 and a second shaft portion 5014, the first shaft portion 5013 is connected between the second shaft portion 5014 and the disc portion 5012, and the disc portion 5012 is on a proximal side of the first shaft portion 5013. As shown in FIGS. 17 and 18, the closure return spring 6 is located between the first closure member 501 and the fixing member 14. In the embodiment, as shown in FIGS. 20 and 27, an annular second stepped surface 5015 is provided between the first shaft portion 5013 and the second shaft portion 5014. The closure return spring 6 is arranged between the second stepped surface 5015 and the fixing member 14. When the first closure member 501 is driven to move proximally, the second stepped surface 5015 compresses the closure return spring 6 to deform. As shown in FIGS. 24 to 27, a first annular stepped surface 50211 is provided on the proximal side of the sleeve portion 5021 of the second closure member 502, the shaft portion is at least partially in the sleeve portion 5021, and the disc portion 5012 is located on the proximal side of the first stepped surface 50211. An outer diameter of the first shaft portion 5013 is smaller than that of the second shaft portion 5014. The first shaft portion 5013 is at least partially in the sleeve portion 5021, and the outer diameter of the second shaft portion 5014 is smaller than an inner diameter of the first stepped surface 50211, so the second shaft portion 5014 can rotate freely relative to the sleeve portion 5021. In the initial state, the first stepped surface 50211 may abut a distal surface of the disc portion 5012 or the first stepped surface 50211 has a certain axial distance from the distal surface of the disc portion 5012. The inner diameter of the first stepped surface 50211 is smaller than the outer diameter of the disc portion 5012. Therefore, when the second pivot portion 422 drives the drive portion 5022 to move proximally, the sleeve portion 5021 moves proximally until the first stepped surface 50211 abuts the distal side of the disc portion 5012, and then the sleeve portion 5021 continues to move proximally, so the disc portion 5012 can drive the first closure member 501 to move proximally as a whole to drive the closure drive piece 12 proximally. The outer diameter of the disc portion 5012 is smaller than the inner diameter of the sleeve portion 5021, so the disc portion 5012 can rotate freely inside the sleeve portion 5021.

Furthermore, in the third to fifth embodiments of the present disclosure, the closure drive mechanism can also automatically open the head assembly. In the third to fifth embodiments, the actuating member includes a switch member. The actuating member is movable between a first region and a second region, and the second region is located at a distal side of the first region.

During the firing process of the stapler, the linkage assembly is maintained in the second state, and the actuating member moves from the first region to the second region in the distal direction. After the stapler is fired, the linkage assembly is in the second state, and when the actuating member is driven to move from the second region to the first region, the switch member drives the linkage assembly away from the actuating member, so the linkage assembly enters the first state, the third pivot portion and the fourth pivot portion move away from the actuating member, and the second pivot portion drives the closure drive piece to move distally through the closure drive assembly to open the head assembly automatically.

Figure 28:
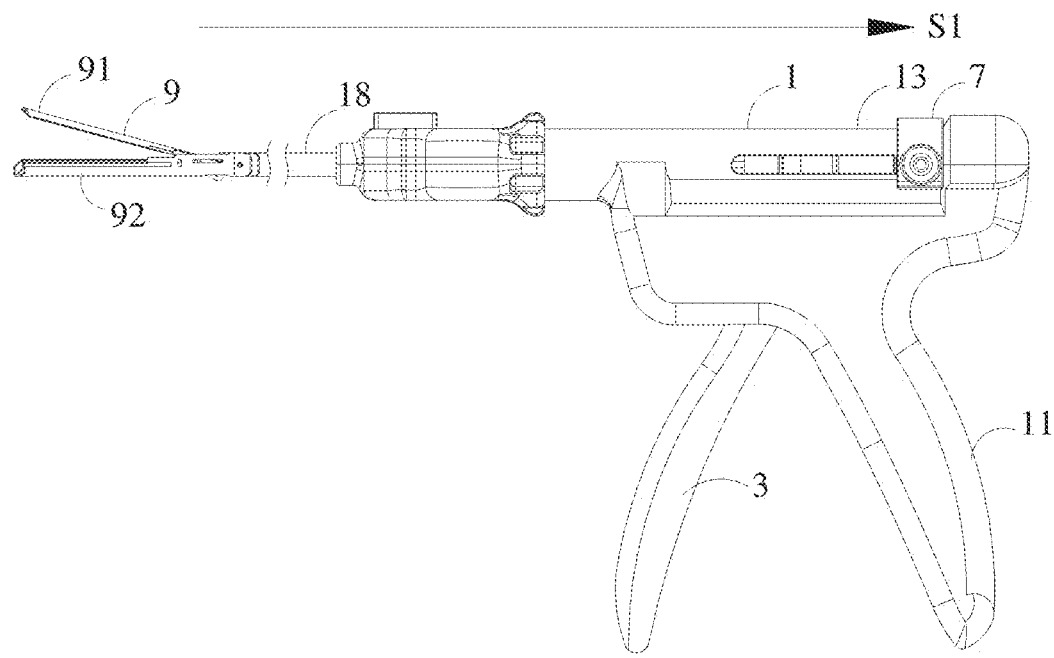
FIG. 28 is a structural schematic view of a stapler according to a third embodiment of the present disclosure.
Figure 36:
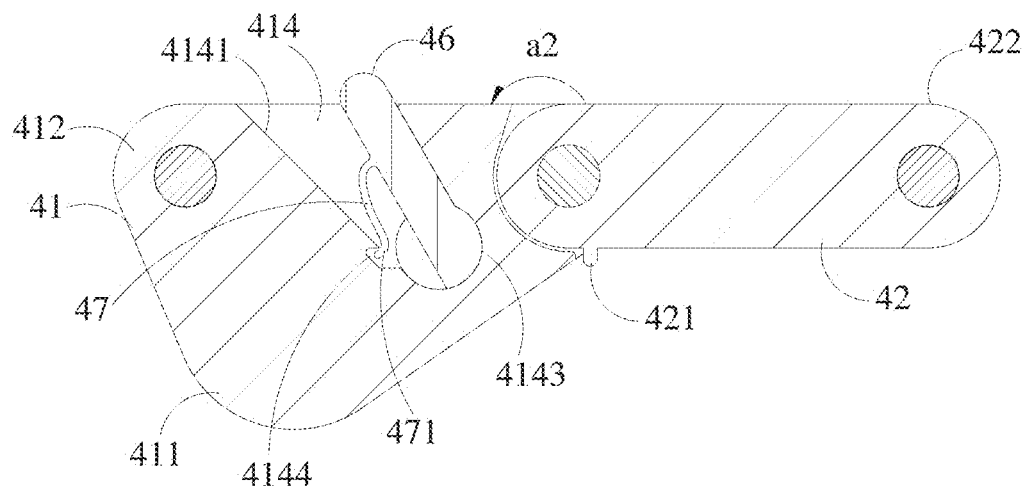
FIG. 36 is a cross-sectional view of the linkage assembly in the second state according to the third embodiment of the present disclosure.
Figure 37:
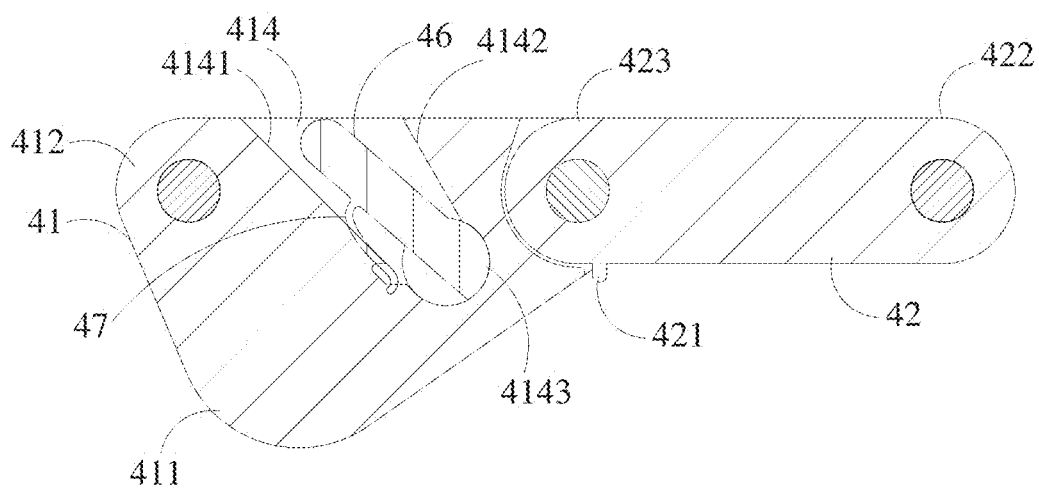
FIG. 37 is a structural schematic view of a first end of the drive member entering a mounting groove according to the third embodiment of the present disclosure.
Figure 38:
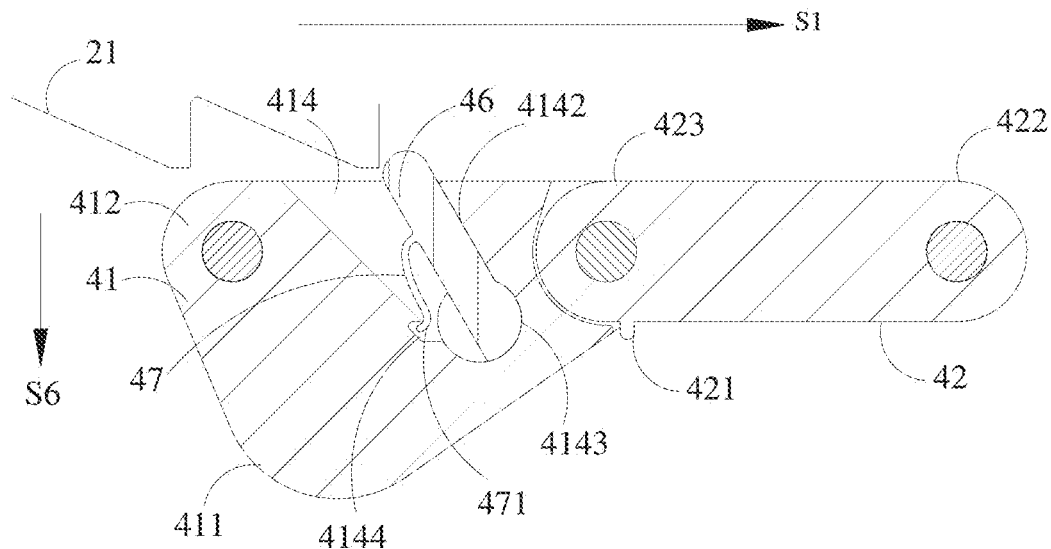
FIG. 38 is a structural schematic view of a toothed rack acting on the drive member according to the third embodiment of the present disclosure.
Figure 39:
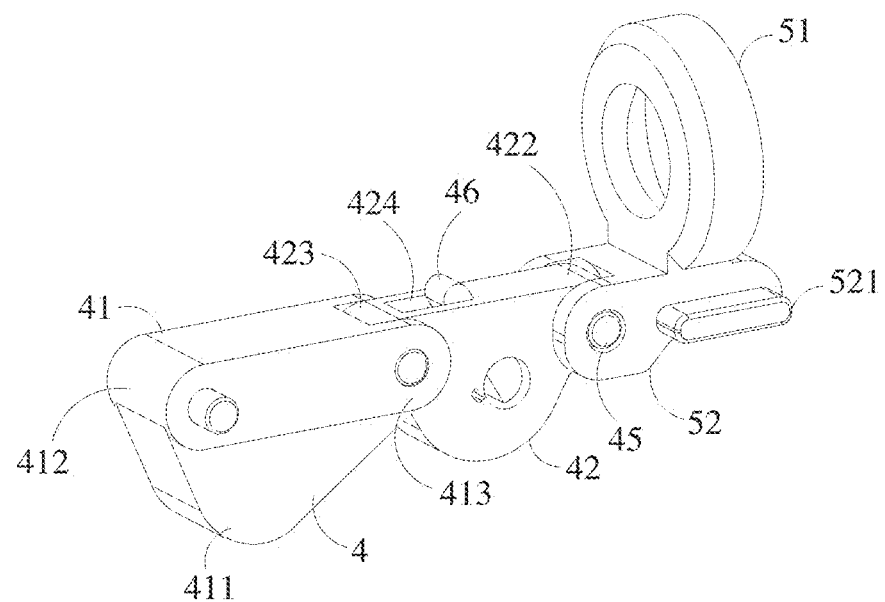
FIG. 39 is a structural schematic view of the linkage assembly cooperating with part of a closure drive assembly according to the third embodiment of the present disclosure.
Figure 40:
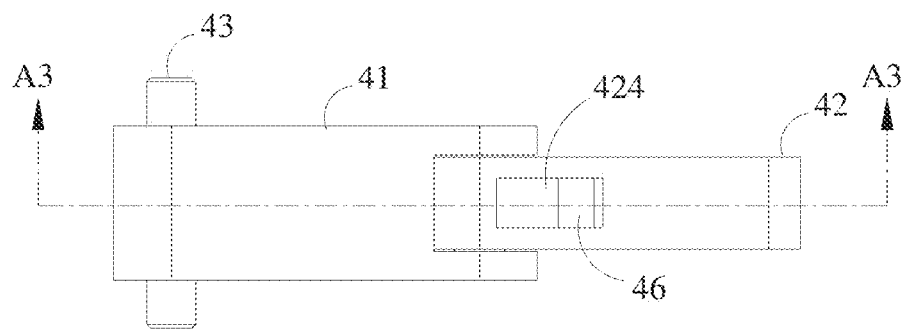
FIG. 40 is a structural schematic view of a linkage assembly in a second state according to a fourth embodiment of the present disclosure.

FIGS. 28 to 38 are structural schematic views of a closure drive mechanism and a surgical stapler according to a third embodiment of the present disclosure. The stapler includes a head assembly 9, an instrument platform 1 and the closure drive mechanism, wherein the head assembly 9 is arranged on a distal side of the instrument platform 1. As shown in FIG. 28 and FIG. 38, the head assembly portion 9 includes an anvil 91 and a cartridge assembly 92 arranged relative to the anvil 91. The anvil 91 has a third state of away from the cartridge assembly 92 and a fourth state close to the cartridge assembly 92. The switching process between the third state and the fourth state of the anvil 91 relative to the cartridge assembly 92 is the same as that of the first embodiment and is not described in detail here. The process of the anvil 91 entering the fourth state from the third state is called the closure process of the head assembly 9, that is, the closure process of the stapler. During the firing process of the stapler, the head assembly 9 needs to be maintained closed. After the stapler is fired, the pivot pin 93 and the closure drive piece 12 move distally to open the head assembly 9.

Figure 29:
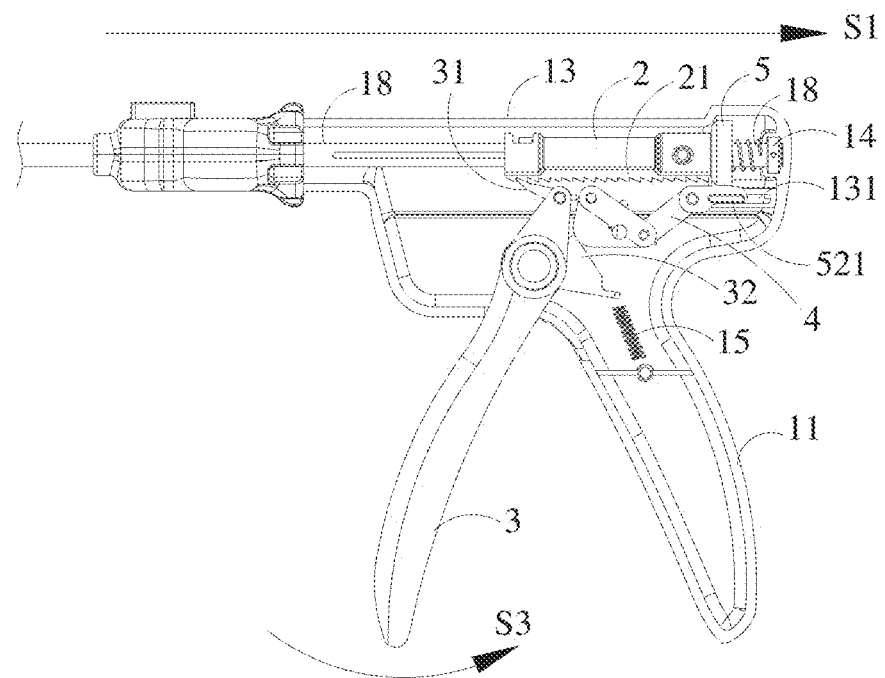
FIG. 29 is a structural schematic view of an instrument platform omitting one side of a housing according to the third embodiment of the present disclosure.
Figure 30:
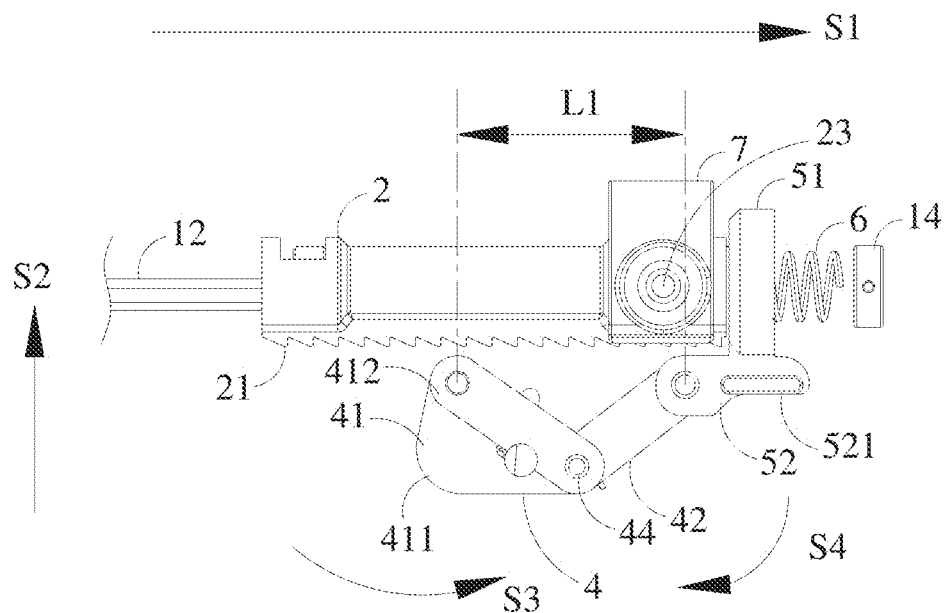
FIG. 30 is a structural schematic view of a linkage assembly in a first state cooperating with other members according to the third embodiment of the present disclosure.
Figure 31:
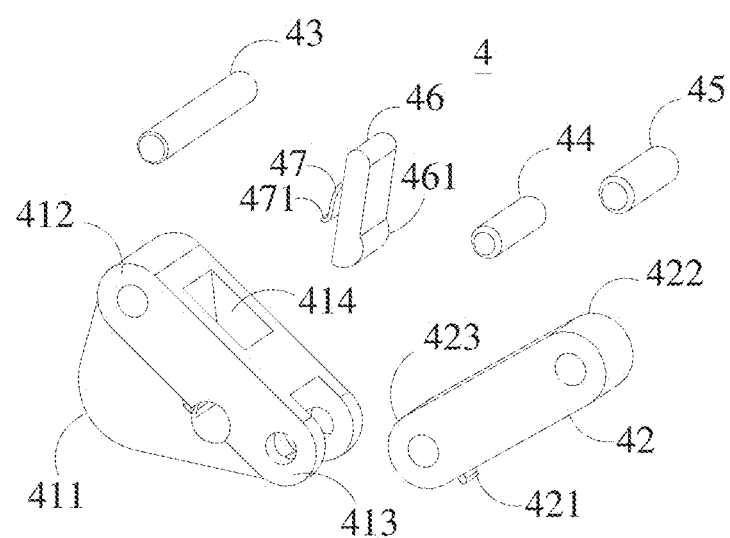
FIG. 31 is an exploded view of the linkage assembly according to the third embodiment of the present disclosure.
Figure 32:
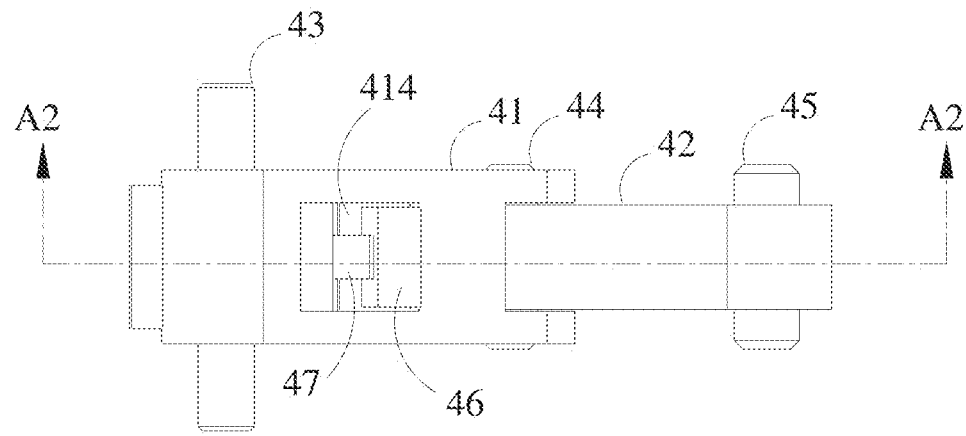
FIG. 32 is a top view of the linkage assembly in the first state according to the third embodiment of the present disclosure.

As shown in FIGS. 29 to 31, the closure drive mechanism further includes a linkage assembly 4, an actuating member 2 and a closure drive assembly 5. The linkage assembly 4 includes a first linkage member 41 and a second linkage member 42 on a proximal side of the first linkage member 41. The first linkage member 41 includes a first pivot portion 412 and a third pivot portion 413. The second linkage member 42 includes a second pivot portion 422 and a fourth pivot portion 423. The cooperation structure between the first linkage member 41 and the second linkage member 42, the cooperation structure between the first linkage member 41 and the housing 13, and the cooperation structure between the second linkage member 42 and the closure drive assembly 5 are the same as those of the first embodiment and are not described in detail herein.

The linkage assembly 4 includes a first state and a second state. When the linkage assembly 4 is in the first state, the second pivot portion 422 is in a third region. When the linkage assembly 4 is in the second state, the second pivot portion 422 is in a fourth region. The fourth region is at a proximal side of the third region. That is, when the linkage assembly 4 enters the second state from the first state, the second pivot portion 422 moves proximally. The actuating member 2 includes a switch member. In this embodiment, the switch member is a toothed rack 21 disposed on one side of the actuating member 2. The actuating member 2 is movable between a first region and a second region, wherein the second region is located at a distal side of the first region.

In this embodiment, the first region refers to the position of the actuating member 2 in the initial state of the stapler, that is, the position of the actuating member 2 as shown in FIG. 29. The second region refers to the region where the actuating member 2 is located after the stapler is fired. During the firing process of the stapler, the movable handle 3 is pressed, and the advancement pawl 31 of the movable handle 3 cooperates with the toothed rack 21 to drive the actuating member 2 to move from the first region to the second region. As shown in FIG. 27, a retract member 7 is fixed on the actuating member 2. During the firing process of the stapler, the retract member 7 moves distally along with the actuating member 2. The actuating member 2 drives the firing rod on the distal side to fire the stapler. After the stapler is fired, the actuating member 2 is in the second region. By operating the retract member 7 to move proximally, the retract member 7 drives the actuating member 2 to return from the second region to the initial first region.

When the linkage assembly 4 enters the second state from the first state, the second pivot portion 422 drives the closure drive piece 12 to move proximally through the closure drive assembly 5 to close the head assembly 9. When the linkage assembly 4 is in the second state and the actuating member 2 moves from the second region to the first region, the switch member drives the linkage assembly 4 away from the actuating member 2, so the linkage assembly 4 enters the first state, wherein the third pivot portion 413 and the fourth pivot portion 423 move away from the actuating member 2, and the second pivot portion 422 drives the closure drive piece 12 to move distally through the closure drive assembly 5 to open the head assembly 9 automatically.

As shown in FIG. 29, the instrument platform includes a housing 13 and a stationary handle 11. The closure drive mechanism further includes a movable handle 3 movably connected to the instrument platform. A return spring 15 is arranged in the instrument platform. The movable handle 3 is provided with an advancement pawl 31 cooperated with the toothed rack 21. The cooperation structure between the movable handle 3 and the first linkage member 41 and the shapes of the first linkage member 41 and the second linkage member 42 are the same as those of the first embodiment, the structure of the closure drive assembly 5 and the cooperation structure between the closure drive assembly 5 and the second linkage member 42 are the same as those of the first embodiment, and are not described in detail here.

As shown in FIGS. 29 to 33, the linkage assembly 4 further includes a drive member 46. A first mounting groove 414 is provided on a side surface of the first linkage member 41 facing the actuating member 2. A second end of the drive member 46 is mounted in the first mounting groove 414, and a first end of the drive member 46 extends outward from a side surface of the first linkage member 41 facing the actuating member 2. The first mounting groove 414 includes a first side wall 4141, a second side wall 4142 and a bottom wall 4143. The first side wall 4141 is located on a distal side of the second side wall 4142. In an initial state, the drive member 46 is located close to the second side wall 4142 of the first mounting hole, and a first gap is formed between the drive member 46 and the first side wall 4141. An elastic member 47 is disposed between the drive member 46 and the first side wall 4141 to bias the drive member 46 toward the second side wall 4142. When the linkage assembly 4 is in the first state, the drive member 46 abuts the second side wall 4142. In this embodiment, the elastic member 47 is an elastic piece, such as a metal elastic piece, a plastic elastic piece, etc. A first end of the elastic piece is connected to the drive member 46, a second end of the elastic piece has a bending portion 471. A side of the first side wall 4141 is provided with a first block groove 4144, and the bending portion 471 is in the first block groove 4144 to maintain the elastic piece stably mounted. The second end of the drive member 46 is pivotally connected to the bottom wall 4143 of the first mounting slot 414. At least part of an outer wall of the second end of the drive member 46 is a first arc-shaped surface 461, and at least part of the bottom wall 4143 of the first mounting groove 414 is a second arc-shaped surface. The first arc-shaped surface 461 fits the second arc-shaped surface, and the first arc-shaped surface 461 is rotatable relative to the second arc-shaped surface. When the linkage assembly 4 is in the second state and the actuating member 2 moves from the second region to the first region, the toothed rack 21 presses the first end of the drive member 46 away from the actuating member 2. In another alternative embodiment, the elastic member 47 may be a spring or other elastic members.

The working principle of the closure drive mechanism is described in detail below with reference to each stage of the working process of the stapler.

Figure 33:
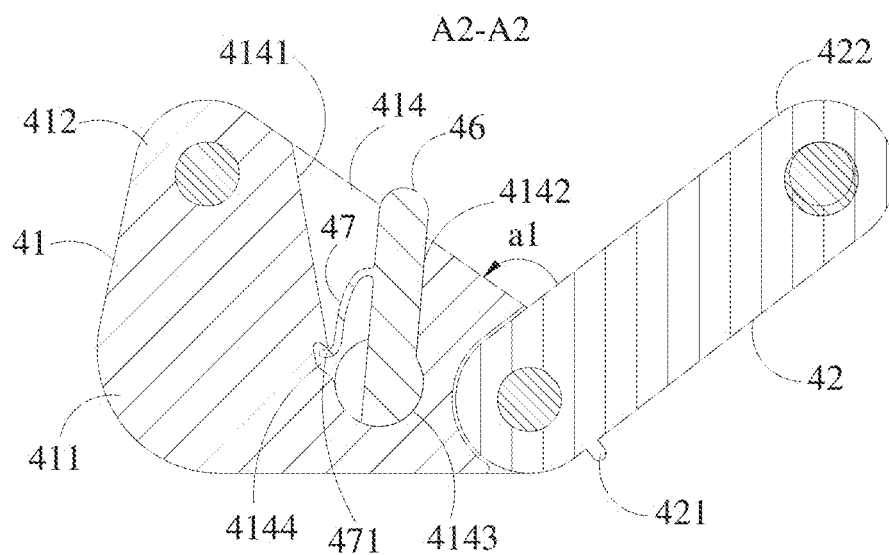
FIG. 33 is a cross-sectional view taken in the direction A2-A2 in FIG. 32.

As shown in FIGS. 29 to 33, in the initial state, the linkage assembly 4 is in the first state, the movable handle 3 is at an initial position away from the stationary handle 11, and the actuating member 2 is in the first region. As shown in FIG. 30, at this time, the third pivot portion 413 and the fourth pivot portion 423 are located relatively away from the actuating member 2. A distance between the center of the first pivot portion 412 and the center of the second pivot portion 422 is L1, and the linkage assembly 4 is in a relatively compact state in the axial direction. As shown in FIG. 33, an angle a1 is formed between the first linkage member 41 and the second linkage member 42. The drive member 46 is arranged close to the second side wall 4142 of the first mounting groove 414, and the first end of the drive member 46 extends outward from the side surface of the first linkage member 41 facing the actuating member 2. As the third pivot portion 413 and the fourth pivot portion 423 are relatively away from the actuating member 2, the toothed rack 21 will not act on the drive member 46. At this time, the outer surface of the second mating portion 411 of the first linkage member 41 abuts the first mating portion 32 of the movable handle 3. The linkage assembly 4 is in a relatively stable state, so when the movable handle 3 is not pressed, the state of the linkage assembly 4 is maintained stable, and the closure drive assembly 5 can be well maintained at its initial position.

Figure 34:
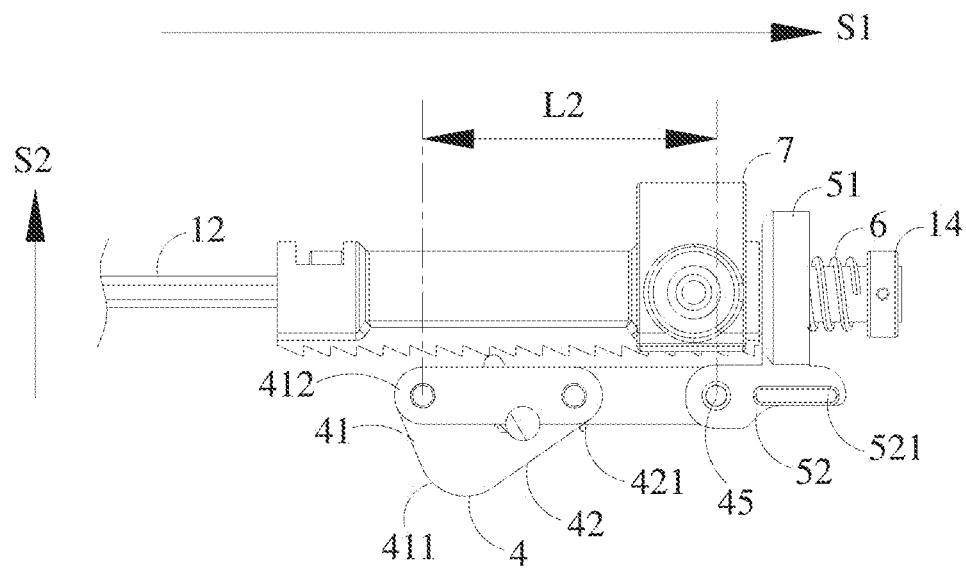
FIG. 34 is a structural schematic view of the linkage assembly in a second state cooperating with other members according to the third embodiment of the present disclosure.
Figure 35:
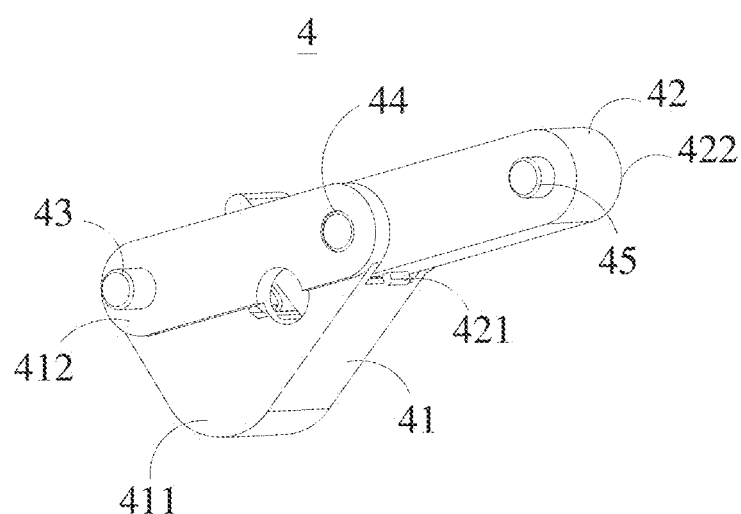
FIG. 35 is a structural schematic view of the linkage assembly in the second state according to the third embodiment of the present disclosure.

After the head assembly 9 reaches the surgical site, the movable handle 3 is pressed to rotate in the first direction, and the second linkage member 42 rotates in the second direction, i.e., direction S4, relative to the first linkage member 41. In the perspective of FIG. 30, the direction S4 is clockwise direction. FIGS. 34 to 36 show the structure of the linkage assembly 4 in the second state.

As shown in FIGS. 34 to 36, during the linkage assembly 4 entering the second state from the first state, the third pivot portion 413 and the fourth pivot portion 423 move toward the actuating member 2 compared to the position in the first state, that is, move upward to a position relatively close to the actuating member 2 in the perspective of FIG. 34. At this time, the linkage assembly 4 is in a relatively stable second state. An axial distance between the center of the first pivot portion 412 and the center of the second pivot portion 422 is L2, and the distance L2 is greater than the axial distance L1 in the first state shown in FIG. 30. The linkage assembly 4 is in a relatively deployed state in the axial direction. As shown in FIG. 36, the angle between the first linkage member 41 and the second linkage member 42 is a2, which is greater than the angle a1 in the first state shown in FIG. 33. As the first pivot portion 412 cannot be moved in the axial direction relative to the housing 13, the second pivot portion 422 moves proximally, and drives the closure drive assembly 5 to move proximally, the sleeve portion 51 compresses the closure return spring 6 to deform, and the closure drive assembly 5 forces the closure drive piece 12 to move proximally to close the head assembly 9.

During the firing process of the stapler, the linkage assembly 4 remains in the second state. When the movable handle 3 is pressed again, the advancement pawl 31 of the movable handle 3 drives the toothed rack 21, so the toothed rack 21 drives the actuating member 2 to move from the first region to the second region at the distal side, and the retract member 7 also moves distally. As shown in FIG. 37, during the firing process of the stapler, the teeth of the toothed rack 21 contact the first end of the drive member 46 and drive the first end of the drive member 46 to move distally, the first end of the drive member 46 at least partially enters the first mounting groove 414, and the elastic member 47 is compressed and elastically deformed. At this time, the drive member 46 doesn't block the toothed rack 21 from moving distally, so the third pivot portion 413 and the fourth pivot portion 423 cannot be forced to move away from the actuating member 2. The linkage assembly 4 can be maintained in the second state to maintain the closure stability of the head assembly 9 and avoid the head assembly 9 from being accidentally opened during the firing process of the stapler.

After the stapler is fired, the actuating member 2 moves to the second region. The toothed rack 21 moves to a distal side of the first end of the drive member 46, and the drive member 46 is no longer affected by the toothed rack 21. Under the deformation restoring force of the elastic member 47, the first end of the drive member 46 rotates proximally and returns to the position shown in FIG. 36. The actuating member 2 is connected to the retract member 7 (shown in FIG. 30) through a fourth shaft 23 (shown in FIG. 30), and a guide slot for guiding the movement of the retract member 7 is provided on the housing 13. When the actuating member 2 moves to the second region, the retract member 7 moves to a distal side of the guide slot. At this time, the operator manually operates the retract member 7 to move toward a proximal end of the guide slot, the retract member 7 drives the actuating member 2 to move proximally. As shown in FIG. 38, when the toothed rack 21 moves from the second region to the first region, the toothed rack 21 presses the drive member 46 away from the actuator rod 2, and the first end of the drive member 46 is blocked by the second side wall 4142 of the first mounting groove 414 and cannot rotate proximally. Therefore, the drive member 46 first blocks the toothed rack 21 from moving proximally. The toothed rack 21 applies a downward force to the first end of the drive member 46, and the third pivot portion 413 and the fourth pivot portion 423 move away from the actuating member 2 (in the direction S6 in FIG. 38), so the linkage assembly 4 enters the first state. At the same time, the second pivot portion 422 drives the closure drive piece 12 to move distally through the closure drive assembly 5 to open the head assembly 9 automatically.

FIGS. 39 to 43 are structural schematic views of part of the closure drive mechanism of a fourth embodiment of the present disclosure. The fourth embodiment is different from the third embodiment only in that a second mounting groove 424 is provided on a side of the second linkage member 42 facing the actuating member 2, and a second end of a drive member 46 is mounted in the second mounting groove 424. The second mounting groove 424 includes a first side wall 4241, a second side wall 4242, and a bottom wall 4243. The first side wall 4241 is located on a distal side of the second side wall 4242. In an initial state, the drive member 46 is disposed close to the second side wall 4242 of the first mounting groove 4244, and a first gap is formed between the drive member 46 and the first side wall 4241. An elastic member 47 is disposed between the drive member 46 and the first side wall 4241. In this embodiment, the elastic member 47 is an elastic piece, such as a metal elastic piece, a plastic elastic piece, etc. A first end of the elastic piece is connected to the drive member 46, and a second end of the elastic piece has a bending portion 471. The end of the first side wall 4241 is provided with a second block groove 4244, and the bending portion 471 enters the second block groove 4244 to maintain the stability of the elastic piece position. At least part of an outer wall of the second end of the drive member 46 is a first arc-shaped surface 461, and at least part of the bottom wall 4243 of the second mounting groove 424 is a second arc-shaped surface. The first arc-shaped surface 461 fits the second arc-shaped surface, and the first arc-shaped surface 461 is rotatable relative to the second arc-shaped surface. When the linkage assembly 4 is in the second state and the actuating member 2 moves from the second region to the first region, the toothed rack 21 forces the first end of the drive member 46 away from the actuating member 2. In another alternative embodiment, the elastic member 47 may be a spring or other kinds of elastic members. The structures of other members in the fourth embodiment, such as the actuating member 2, the movable handle 3, the connecting rod 18, the closure drive piece 12, the closure drive assembly 5, the instrument platform 1, the head assembly 9, etc., may be the same as those in the third embodiment, or may be different from the third embodiment and adopt other structures, all of which fall within the protection scope of the present disclosure.

Figure 41:
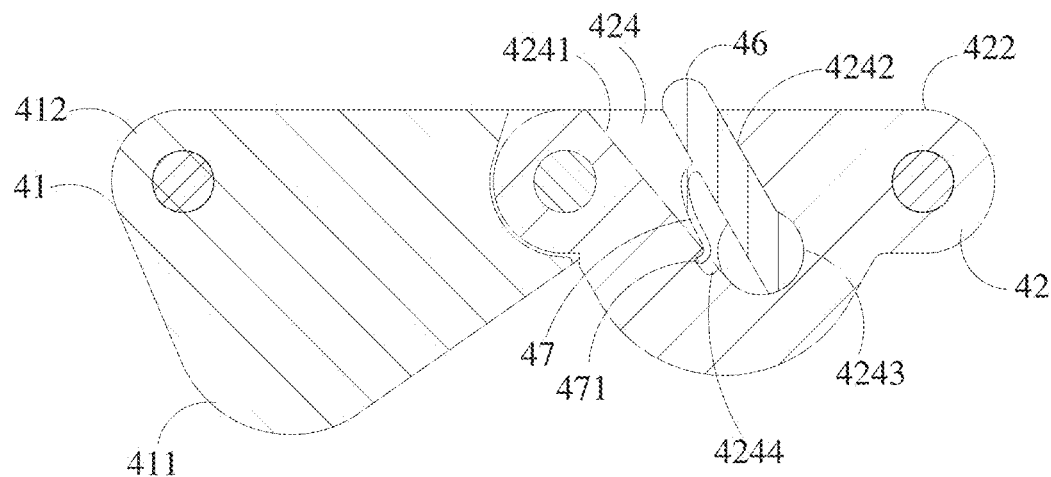
FIG. 41 is a cross-sectional view taken in direction A3-A3 in FIG. 40.
Figure 42:
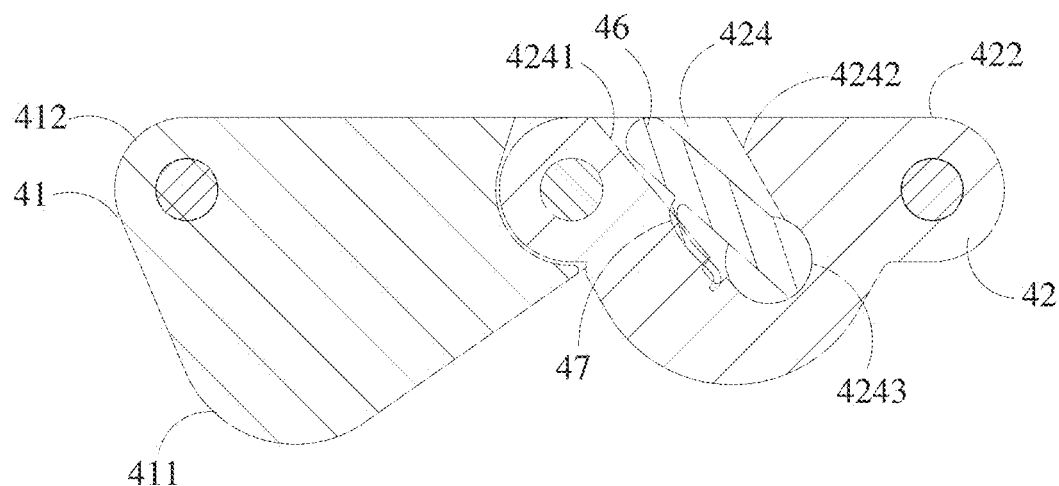
FIG. 42 is a structural schematic view of a first end of a drive member entering a mounting groove according to the fourth embodiment of the present disclosure.
Figure 43:
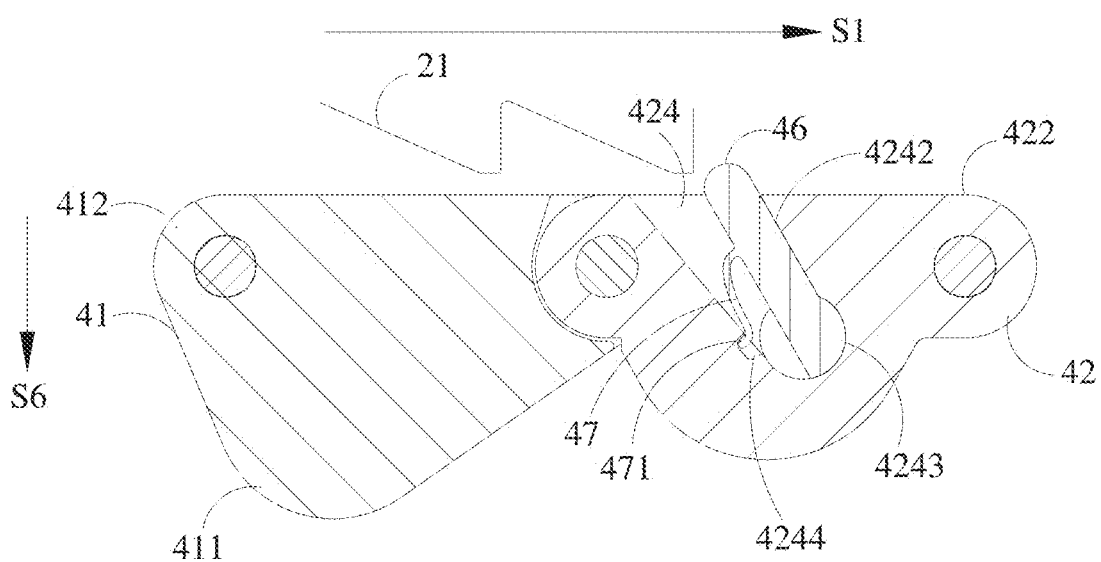
FIG. 43 is a structural schematic view of a toothed rack acting on the drive member according to the fourth embodiment of the present disclosure.

The principle of closing the stapler in the fourth embodiment is the same as that in the third embodiment. FIG. 41 shows the structure when the linkage assembly is in the second state and the toothed rack 21 does not act on the drive member 46, at this time the first end of the drive member 46 extends outward from a side surface of the second linkage member 42 facing the actuating member 2. As shown in FIG. 42, during the firing process of the stapler, the toothed rack 21 drives the first end of the drive member 46 to move distally and at least partially enter the second mounting groove 424 so as not to block the toothed rack 21 from moving distally. As shown in FIG. 43, after the stapler is fired, the retract member 7 is forced proximally, the toothed rack 21 moves proximally and acts on the first end of the drive member 46, the toothed rack 21 forces the drive member 46 away from the actuating member 2, so the third pivot portion 413 and the fourth pivot portion 423 move away from the actuating member 2, and the linkage assembly 4 returns to the first state. At the same time, the second pivot portion 422 drives the closure drive piece 12 to move proximally through the closure drive assembly 5 to open the head assembly automatically.

Figure 44:
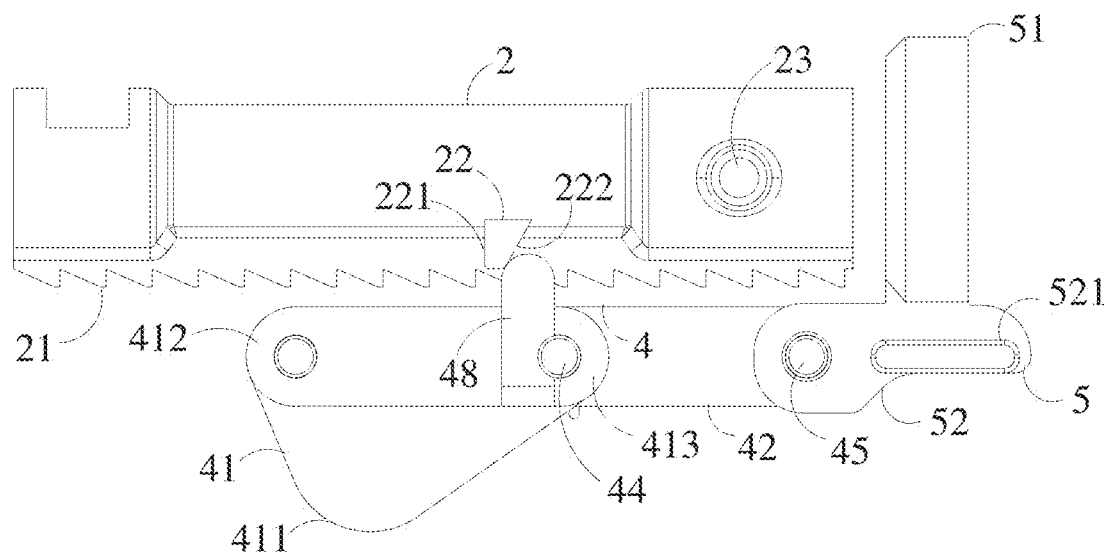
FIG. 44 is a structural view of part of a closure drive mechanism according to a fifth embodiment of the present disclosure.
Figure 45:
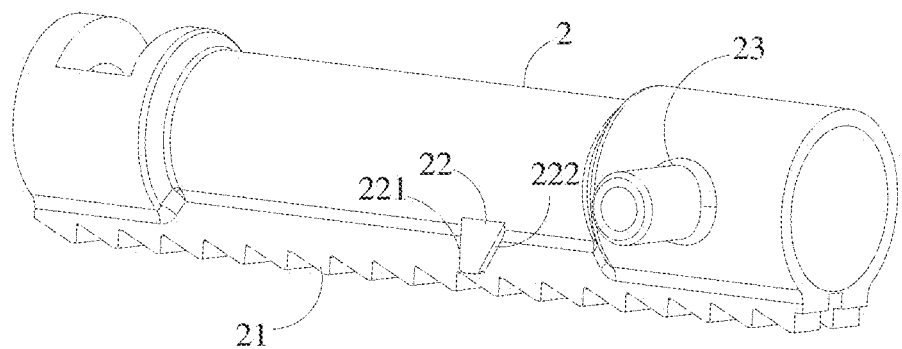
FIG. 45 is a structural schematic view of an actuating member according to the fifth embodiment of the present disclosure.
Figure 46:
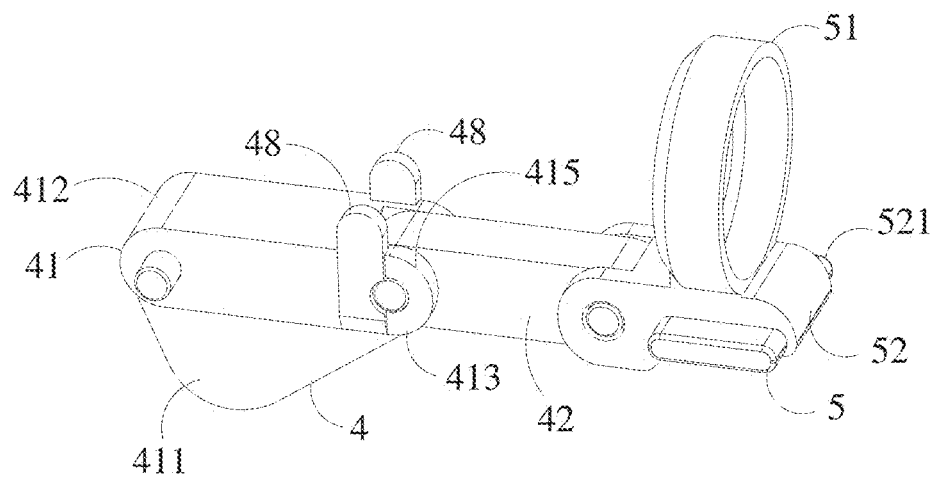
FIG. 46 is a structural schematic view of a linkage assembly cooperating with part of a closure drive assembly according to the fifth embodiment of the present disclosure.
Figure 47:
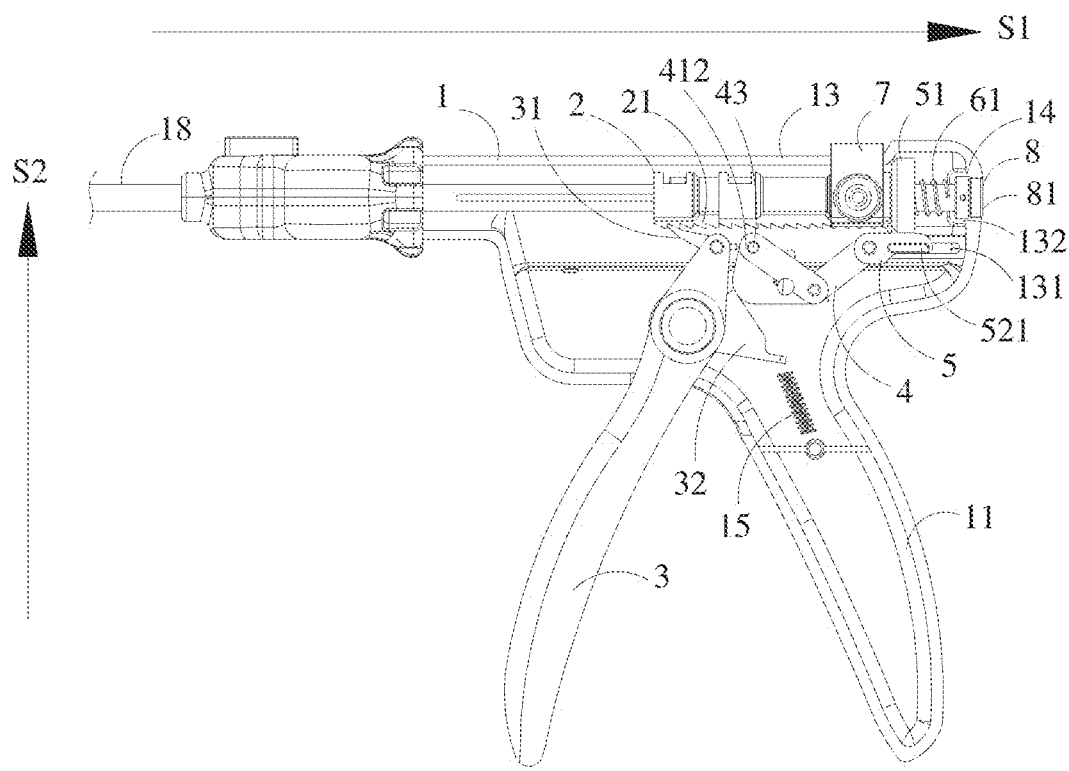
FIG. 47 is a structural schematic view of an instrument platform omitting one side of a housing according to a sixth embodiment of the present disclosure.

FIGS. 44 to 46 are structural schematic views of part of the closure drive mechanism of a fifth embodiment of the present disclosure. The fifth embodiment is different from the third embodiment in that at least one side of the first linkage member 41 is provided with a drive member 48, and the drive member 48 is rotatably connected to a side wall of the first linkage member 41, and the switch member is a drive tooth 22 provided on at least one side of the actuating member 2. As shown in FIG. 45 and FIG. 46, in this embodiment, each of two sides of the first linkage member 41 is provided with the drive member 48, and the drive tooth 22 is disposed on each of two sides of the actuating member 2. The drive tooth 22 includes a first side wall 221 and a second side wall 222. The first side wall 221 of the drive tooth 22 is located on a distal side of the second side wall 222. The first side wall 221 of the drive tooth 22 is a vertical surface, and the second side wall 222 of the drive tooth 22 is a guide surface. A proximal side of the guide surface is inclined upward compared to a distal side thereof. In another alternative embodiment, the drive member 48 may be provided on only one side of the first linkage member 41, and the drive tooth 22 may be provided on one side of the actuating member 2.

In this embodiment, the drive member 48 is disposed on the third pivot portion 413, and a first end of the drive member 48 is rotatable around the second shaft 44 toward the distal side. The first linkage member 41 is further provided with a block portion 415 on a proximal side of the drive member 48, and the block portion 415 blocks the second end of the drive member 48 from moving proximally. A torsion spring is jacketed on the second shaft 44, and the torsion spring abuts both the drive member 48 and the first linkage member 41. In other embodiments, the drive member 48 may also cooperate with other kinds of elastic members.

The principle of closing the stapler in the fifth embodiment is the same as that in the third embodiment. During the firing process of the stapler, when the drive tooth 22 moves from the proximal side to the distal side of the drive member 48, the drive tooth 22 drives the first end of the drive member 48 to rotate distally so as not to block the drive tooth 22 from moving distally, and the torsion spring is elastically deformed. After the stapler is fired, the retract member 7 is moved proximally, so the drive tooth 22 moves proximally along with the actuating member 2, and the drive tooth 22 acts on the drive member 48. The drive member 48 is blocked by the block portion 415 and cannot move proximally. The drive tooth 22 applies a force to the first end of the drive member 48 away from the actuating member 2, so the third pivot portion 413 and the fourth pivot portion 423 move away from the actuating member 2, and the linkage assembly 4 returns to the first state. At the same time, the second pivot portion 422 drives the closure drive piece 12 to move proximally through the closure drive assembly 5 to open the head assembly automatically.

Furthermore, due to the existence of structural tolerances of dimension chain of the stapler, the closure drive piece may not retract to its initial position after the stapler is opened. Therefore, the head assembly needs to be manually opened by operating a reset member to move distally to drive the closure drive piece to move distally, so the situation where the closure drive piece fails to retract to its initial position and the head assembly cannot be opened normally is avoided. In a sixth and a seventh embodiments of the present disclosure, a structure for manually opening the head assembly by a reset member is further provided. Specifically, in the sixth embodiment and the seventh embodiment, the closure drive mechanism further includes the reset member on the proximal side of the connecting rod. The reset member is at least partially in the connecting rod and movable in the axial direction relative to the connecting rod.

FIGS. 47 to 59 are structural schematic views of a closure drive mechanism and a surgical stapler including the same according to the sixth embodiment of the present disclosure. The cooperation between the head assembly and the instrument platform in this embodiment is the same as that in the first embodiment. With reference to FIG. 1 of the first embodiment, the stapler includes a head assembly 9, an instrument platform and a closure drive mechanism, wherein the closure drive mechanism is used to close and open the head assembly 9, and the head assembly 9 is located on a distal side of the instrument platform 1. The instrument platform 1 includes a housing 13 and a stationary handle 11 on one side of the housing 13. With reference to FIGS. 1 and 2 of the first embodiment, the head assembly 9 includes an anvil 91 and a cartridge assembly 92 arranged relative to the anvil 91, and the anvil 91 has a third state away from the cartridge assembly 92 and a fourth state close to the cartridge assembly 92. The switch between the third state and the fourth state of the anvil 91 relative to the cartridge assembly 92 is the same as that in the first embodiment and is not described in detail here.

As shown in FIGS. 47 to 50, the closure drive mechanism further includes a connecting rod 18 and a reset member 8. The connecting rod 18 extends along the axial direction of the stapler. The closure drive piece 12 is at least partially in the connecting rod 18 and is movable in the axial direction relative to the connecting rod 18. A first stop portion is disposed on a proximal side of the closure drive piece 12. The reset member 8 is located on a proximal side of the connecting rod 18, and the reset member 8 includes an operating portion 81 and a reset mating portion 82. The reset mating portion 82 of the reset member 8 is at least partially in the connecting rod 18 and is movable in the axial direction relative to the connecting rod 18. The operating portion 81 is connected to a proximal side of the reset mating portion 82, and a proximal surface of the operating portion 81 is a surface suitable for an operator to press. In the initial state, the reset mating portion 82 abuts the first stop portion. If the closure drive piece 12 moves proximally, the first stop portion can drive the reset mating portion 82 to move proximally. At the same time, when the head assembly needs to be manually opened, the operating portion 81 of the reset member 8 is moved distally, the reset mating portion 82 abuts the first stop portion, and drives the closure drive piece 12 to move distally, so the head assembly can be manually opened. Therefore, the situation that the closure drive piece 12 fails to retract to its initial position and the head assembly cannot be opened normally is avoided.

Figure 48:
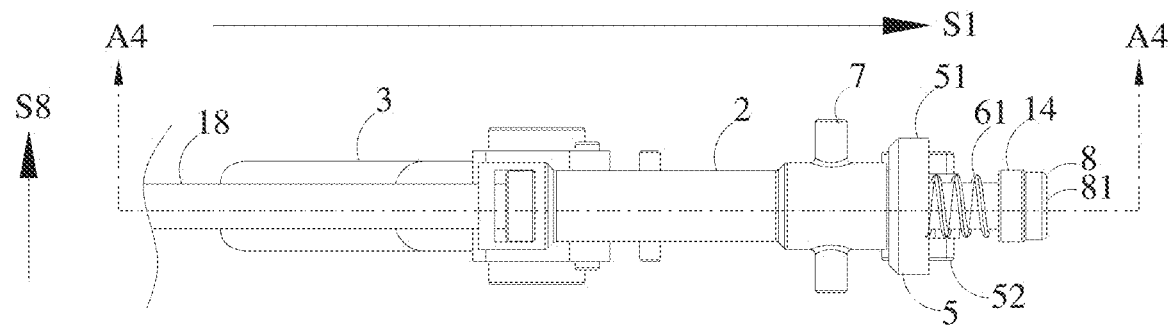
FIG. 48 is a top view of a closure switch mechanism according to the sixth embodiment of the present disclosure.

As shown in FIGS. 47 to 50, the closure drive mechanism further includes a second stop portion. The second stop portion is on a proximal side of the first stop portion and fixed to the housing 13 of the instrument platform in the axial direction. When the reset member 8 is driven to move proximally, the second stop portion stops the reset member 8 from continuing to move. The housing 13 of the instrument platform of the stapler is provided with a mating portion for the second stop portion, and the second stop portion is rotatably provided on the mating portion. In this embodiment, the second stop portion is a first connecting pin 19. The mating portion for the second stop portion is a circumferential groove 132 provided on the inner surface of the housing 13, and the first connecting pin 19 is rotatably provided in the circumferential groove 132. Here, the first connecting pin 19 rotating means that the first connecting pin 19 rotates around an axis of the first connecting pin 19. Direction S8 in FIG. 48 is the lateral direction of the stapler, that is, the width direction.

Figure 50:
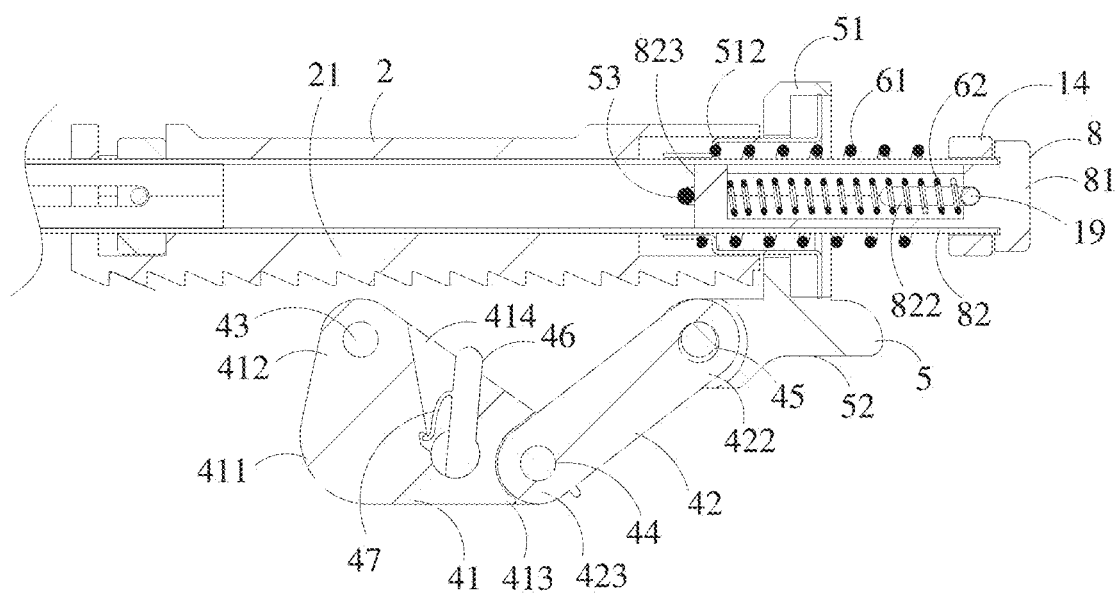
FIG. 50 is a schematic view of FIG. 49 omitting the movable handle.

As shown in FIG. 50, the operating portion 81 is located on a proximal side of the first connecting pin 19, and the first connecting pin 19 is at least partially in the reset mating portion 82. In the embodiment, a sliding slot 822 extending in the axial direction is provided on a side surface of the reset mating portion 82, and the first connecting pin 19 is at least partially in the sliding slot 822 and movable along an extension direction of the sliding slot 822. Through the cooperation between the first connecting pin 19 and the sliding slot 822, the reset mating portion 82 is limited to be only movable in the axial direction relative to the first connecting pin 19, that is, the reset mating portion 82 cannot move laterally or longitudinally relative to the first connecting pin 19, and cannot rotate relative to the first connecting pin 19. The sliding slot 822 is not connected to the distal end and the proximal end of the reset mating portion 82, so the first connecting pin 19 is ensured not to be separated from the reset mating portion 82 from the distal end or the proximal end of the sliding slot 822.

In the sixth embodiment shown in FIGS. 47 to 50, the closure drive mechanism further includes an annular fixing member 14 on the proximal side of the connecting rod 18. The housing 13 of the instrument platform 1 is provided with a fixing member mounting hole 132 shaped to fit the fixing member 14, and the fixing member 14 is fixed in the fixing member mounting hole 132 to fixedly connect the fixing member 14 to the housing 13 of the instrument platform 1. The operating portion 81 of the reset member 8 is on a proximal side of the fixing member 14, the reset mating portion 82 passes through the fixing member 14, and the reset mating portion 82 is movable in the axial direction relative to the fixing member 14. The longitudinal position and the lateral position of the reset member 8 are further limited by the fixing member 14, so the reset member 8 is only movable in the axial direction relative to the housing 13 of the instrument platform 1. In this embodiment, an outer diameter of the reset mating portion 82 is smaller than an inner diameter of the fixing member 14, and an outer diameter of the operating portion 81 is larger than the inner diameter of the fixing member 14, so the operating portion 81 can be maintained on the proximal side of the fixing member 14 without entering the fixing member 14.

As shown in FIGS. 47 to 50, in this embodiment, the first stop portion is a second connecting pin 53. The closure drive mechanism may further include a structure for driving the head assembly to close. In the embodiment, the closure drive mechanism further includes a movable handle 3, a linkage assembly 4 and a closure drive assembly 5. The movable handle 3 is pivotally connected to the housing 13 of the instrument platform 1. The movable handle 3 includes a first mating portion 32. A return spring 15 is provided between the movable handle 3 and the housing of the stapler. When the movable handle 3 is pressed to rotate toward the stationary handle 11, the return spring 15 is elastically deformed. The linkage assembly 4 includes a first linkage member 41 and a second linkage member 42 on a proximal end of the first linkage member 41. The first linkage member 41 includes a first pivot portion 412, and the second linkage member 42 includes a second pivot portion 422. The linkage assembly 4 includes two relatively stable states: a first state corresponding to the head assembly being opened and a second state corresponding to the head assembly being closed. The cooperation structure of the movable handle 3, the first linkage member 41, the second linkage member 42, the closure drive assembly 5 and the housing 13 is the same as that of the first embodiment and is not described in detail herein.

Figure 56:
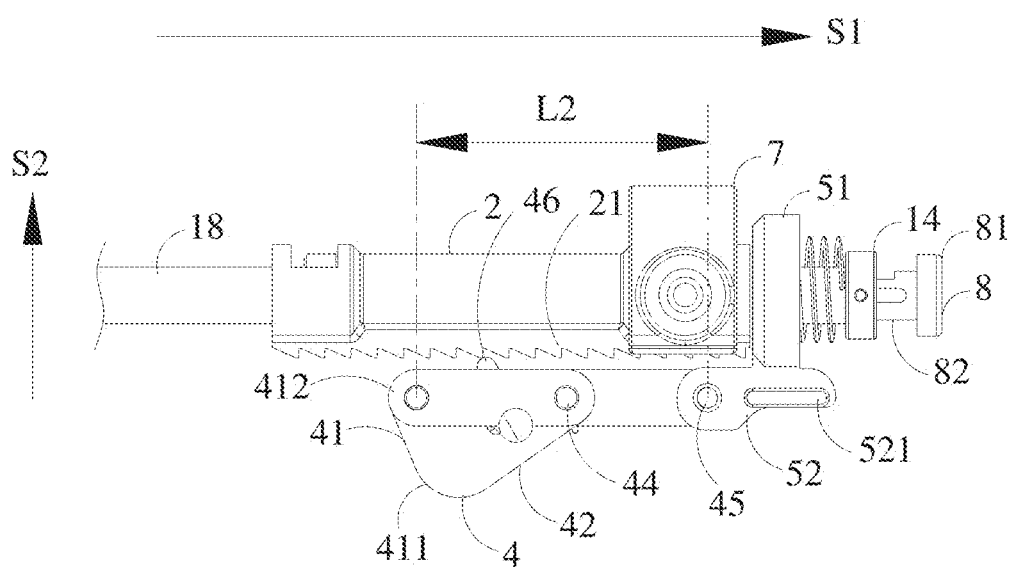
FIG. 56 is a structural schematic view of the linkage assembly in the second state cooperating with other members according to the sixth embodiment of the present disclosure.
Figure 57:
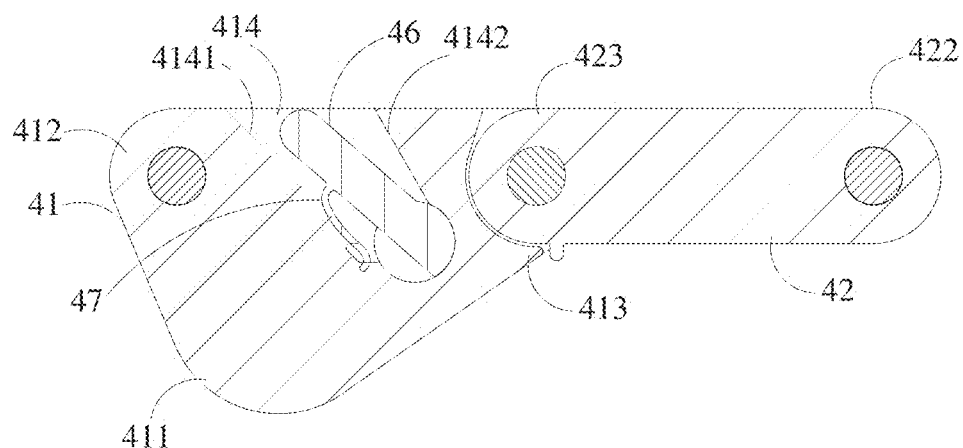
FIG. 57 is a cross-sectional view of the linkage assembly in the second state according to the sixth embodiment of the present disclosure.
Figure 58:
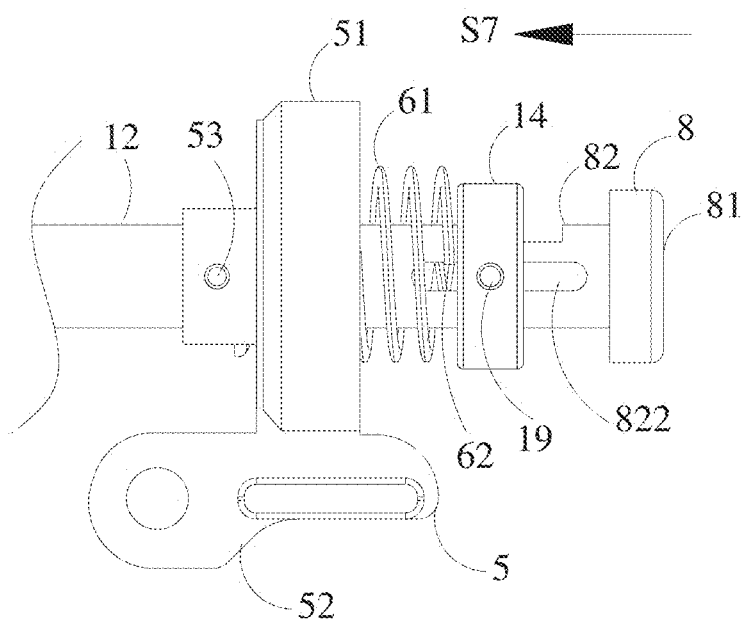
FIG. 58 is a schematic view of a state of a reset member after the head assembly is closed according to the sixth embodiment of the present disclosure.
Figure 59:
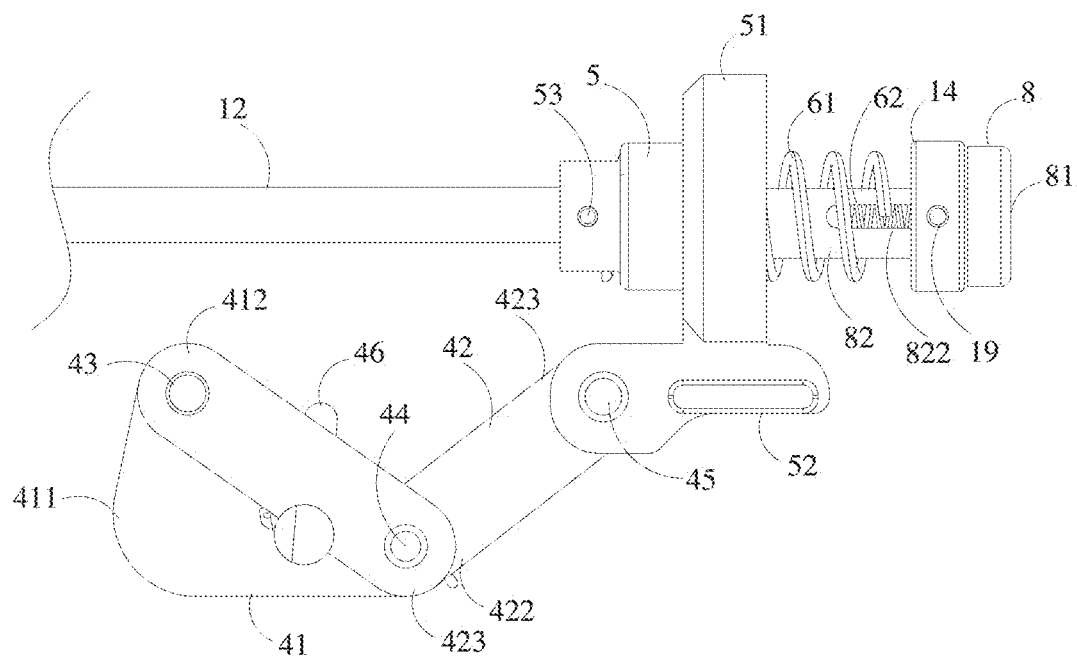
FIG. 59 is a structural schematic view of the closure drive mechanism when the reset member is driven to open the head assembly according to the sixth embodiment of the present disclosure.

The structure of the closure drive mechanism of the sixth embodiment in different states is described in detail below with reference to FIGS. 47 to 59. FIGS. 47 to 55 show the structure of the closure drive mechanism when the head assembly is open, wherein the linkage assembly 4 is in the first state. FIGS. 56 to 58 show the structure of the closure drive mechanism when the head assembly is closed, wherein the linkage assembly 4 is in the second state. FIG. 59 shows the structure of the closure drive mechanism after the head assembly is opened again by the closure drive mechanism in this embodiment, wherein the linkage assembly 4 returns to the first state.

Figure 51:
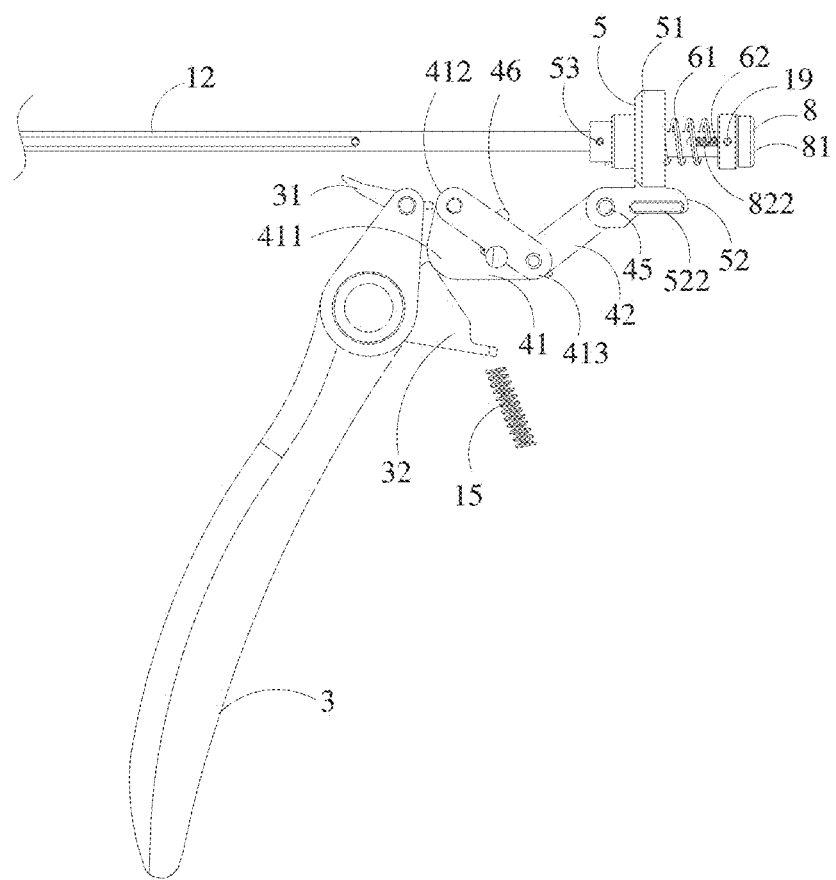
FIG. 51 is a structural schematic view of a closure drive mechanism according to the sixth embodiment of the present disclosure.
Figure 52:
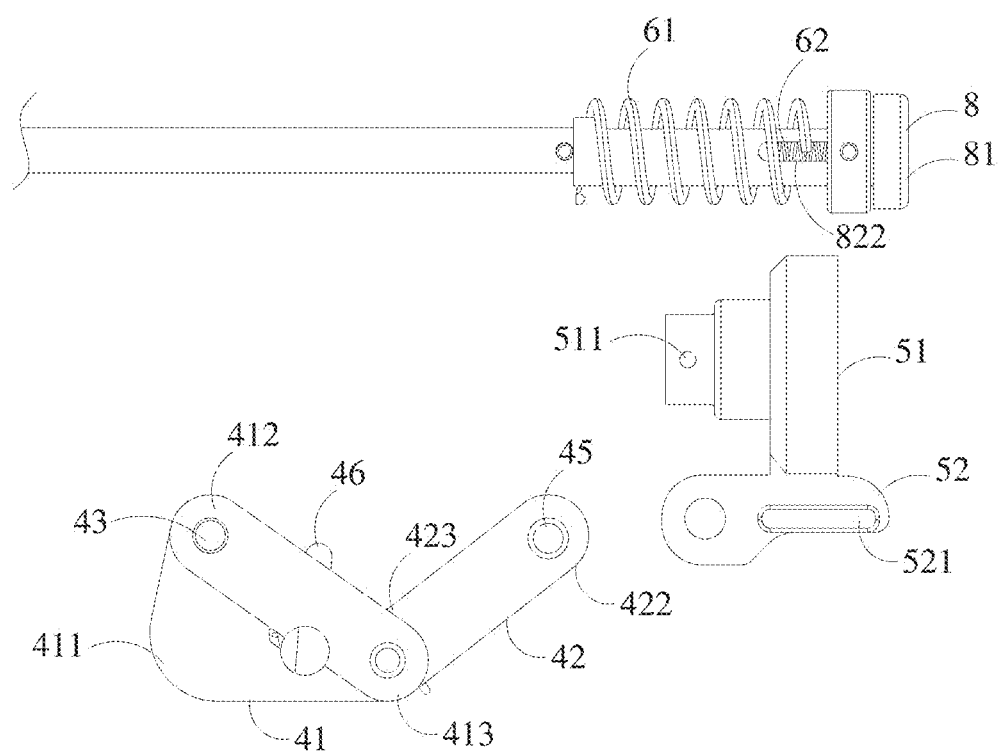
FIG. 52 is an exploded view of the closure drive mechanism omitting the movable handle according to the sixth embodiment of the present disclosure.

As shown in FIGS. 50 to 52, in the initial state, the linkage assembly 4 is in the first state. The linkage assembly 4 is in a relatively compact state. The distance between the first pivot portion 412 and the second pivot portion 422 of the linkage assembly 4 is small. The third pivot portion 413 and the fourth pivot portion 423 are located at a position away from the connecting rod 18. The closure drive assembly 5 includes a sleeve portion 51 and a drive portion 52. The sleeve portion 51 is jacketed on the connecting rod 18 and is movable in the axial direction relative to the connecting rod 18. A through bore 511 is provided on a distal side of the sleeve portion 51. The second connecting pin 53 passes through the through bore 511 to fixedly connect a distal side of the sleeve portion 511 and the proximal side of the closure drive piece 12. The drive portion 52 is located on a side of the sleeve portion 51 facing the linkage assembly 4, and one end of the drive portion 52 is pivotally connected to the second pivot portion 422 of the linkage assembly 4. A second biasing member is further provided between the sleeve portion 51 and the first connecting pin 19, and the second biasing member biases the sleeve portion 51 distally. In the embodiment, the second biasing member is a second return spring 61. The second return spring 61 is located between the stepped surface 512 inside the sleeve portion 51 and the first connecting pin 19. The second return spring 61 may be a compression spring, for example.

Figure 53:
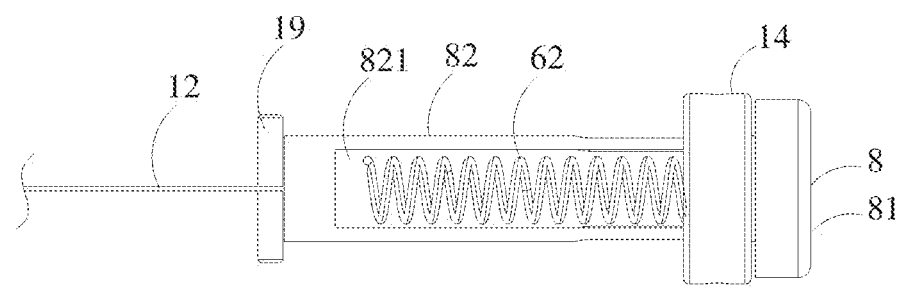
FIG. 53 is a top view of the reset member cooperating with the fixing member according to the sixth embodiment of the present disclosure.
Figure 54:
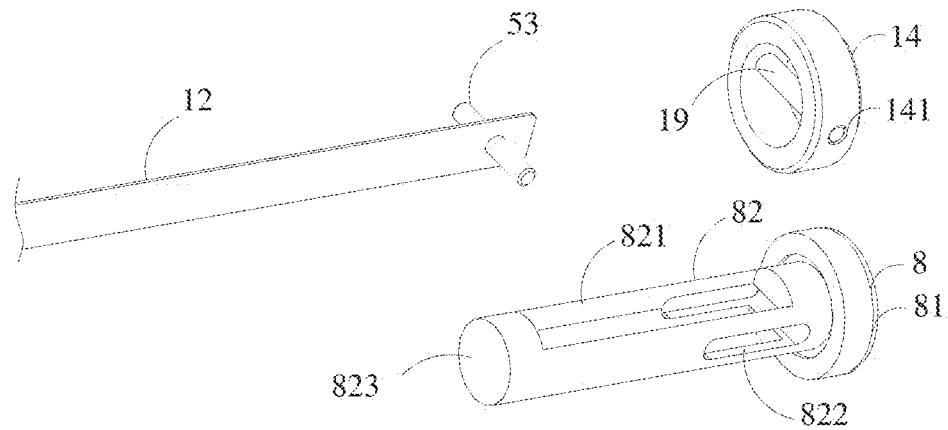
FIG. 54 is an exploded view of the reset member cooperating with the second stop portion according to the sixth embodiment of the present disclosure.

As shown in FIGS. 52 to 54, a pin hole 141 is provided on a side wall of the fixing member 14, and the first connecting pin 19 passes through both the fixing member 14 and the pin hole 141.

In this embodiment, a first biasing member is provided between the reset mating portion 82 and the first connecting pin 19, and the first biasing member biases the reset mating portion 82 distally. In the embodiment, as shown in FIGS. 50 and 53, the first biasing member is a first return spring 62, a cavity is provided in the return mating portion 82, and the first return spring 62 is arranged inside the cavity. In a selective embodiment, a first end of the first return spring 62 abuts a distal side of the cavity, and a second end of the first return spring 62 abuts the first connecting pin 19 to maintain the return button 8 in a stable state. The first return spring 62 may be, for example, a compression spring. A spring mounting hole 821 may be provided on an upper surface of the cavity for mounting the first return spring 62 inside the cavity of the return mating portion 82.

Figure 55:
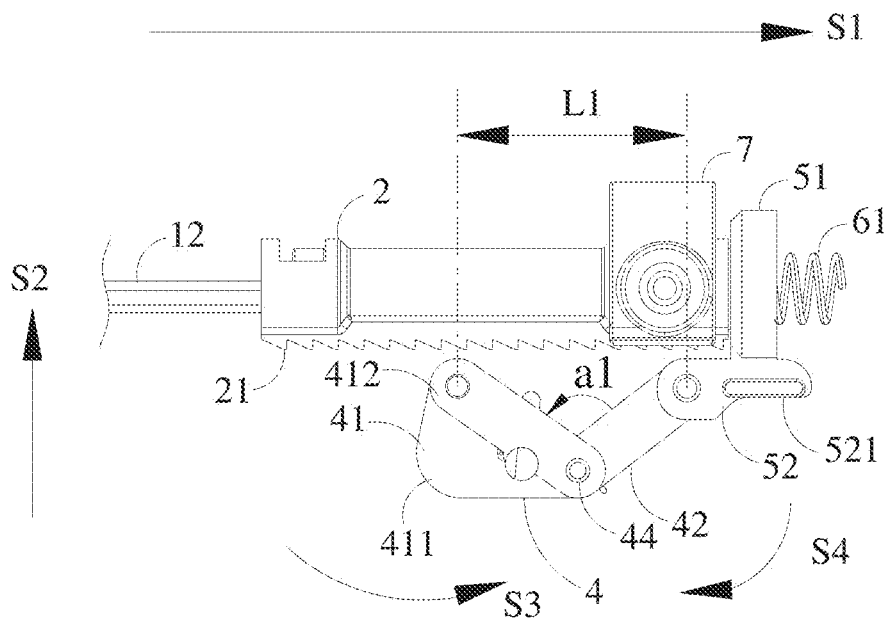
FIG. 55 is a structural schematic view of the linkage assembly in the first state cooperating with other members according to the sixth embodiment of the present disclosure.

As shown in FIGS. 50, 51 and 55, when the linkage assembly 4 is in the first state, the axial distance between the first pivot portion 412 and the second pivot portion 422 of the linkage assembly 4 is L1, and the angle between the first linkage member 41 and the second linkage member 42 is a1. When the movable handle 3 rotates in the first direction (counterclockwise in FIG. 51), the first mating portion 32 of the movable handle 3 cooperates with the second mating portion 411 of the first linkage member 41, and drives the first linkage member 41 to rotate around the first shaft 43 in the direction S3 (counterclockwise in FIG. 55), and the second linkage member 42 rotates around the second pin 44 in the direction S4 (clockwise in FIG. 55), so the distance between the second pivot portion 422 and the first pivot portion 412 gradually increases, the angle between the first linkage member 41 and the second linkage member 42 gradually increases, the third pivot portion 413 and the fourth pivot portion 423 move toward the connecting rod 18, and the linkage assembly 4 enters the second state as shown in FIG. 56. As shown in FIGS. 55 and 56, after the linkage assembly 4 is in the second state, the axial distance between the second pivot portion 422 and the first pivot portion 412 increases from L1 to L2, and the angle between the first linkage member 41 and the second linkage member 42 also increases to an angle approximately equal to 180°. As the first pivot portion 412 cannot move in the axial direction relative to the housing 13 of the instrument platform 1, the position of the second pivot portion 422 in the second state is at a proximal side of the position of the second pivot portion 422 in the first state, and the second pivot portion 422 drives the closure drive assembly 5 to move proximally. At this time, the linkage assembly 4 is maintained in a relatively stable second state. Even if the movable handle 3 is released at this time, the movable handle 3 returns to its initial position under the action of the return spring 15, and the state of the linkage assembly 4 will not change.

As shown in FIGS. 56 to 58, when the linkage assembly 4 enters the second state from the first state, as the closure drive assembly 5 moves proximally, the closure drive assembly 5 drives the closure drive piece 12 to move proximally through the second connecting pin 53 to close the head assembly. At the same time, the second connecting pin 53 abuts a distal surface 823 of the reset mating portion 82 and drives the reset mating portion 82 to move proximally, and the reset member 8 moves proximally as a whole until an axial distance is formed between the distal end of the operating portion 81 and the proximal end of the fixing member 14, and the operating portion 81 extends outward from the proximal side of the housing 13 of the stapler. At this time, the reset mating portion 82 of the reset member 8 compresses the first return spring 62 to deform, and the sleeve portion 51 of the closure drive assembly 5 compresses the second return spring 61 to deform.

Figure 49:
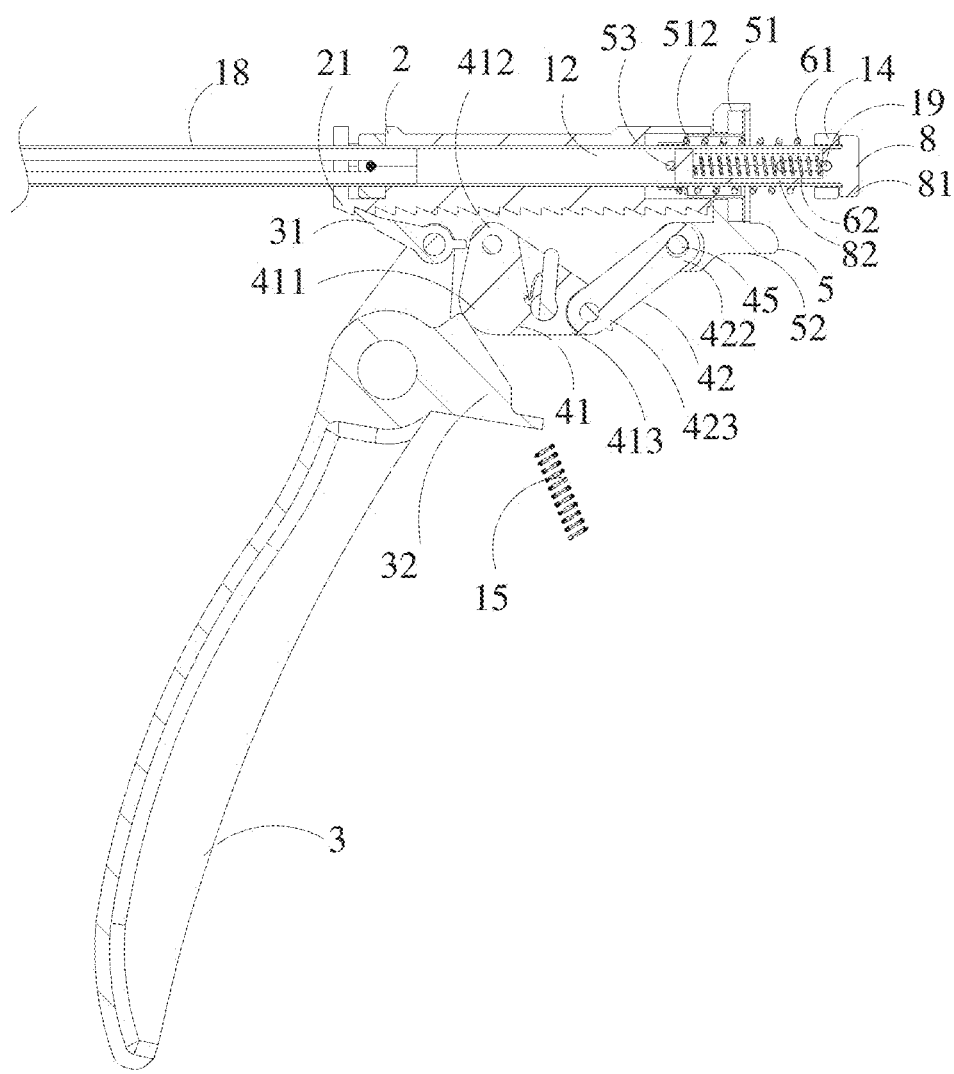
FIG. 49 is a cross-sectional view taken in direction A4-A4 in FIG. 4.

In this embodiment, the closure drive mechanism may further include a structure for automatically opening the head assembly after the head assembly is closed. In the embodiment, the linkage assembly 4 further includes a drive member 46, and the closure drive mechanism further includes a switch member. In this embodiment, the closure drive mechanism further includes an actuating member 2 jacketed on the connecting rod 18. A toothed rack 21 is provided on a side of the actuating member 2 facing the linkage assembly 4. The toothed rack 21 functions as both an actuation member for firing the stapler and a switch member. The toothed rack 21 is movable between a first region and a second region, wherein the first region is at a proximal side of the second region. In an initial state, the toothed rack 21 is in the first region. As shown in FIG. 49, the movable handle 3 further includes an advancement pawl 31 cooperated with the toothed rack 21. After the head assembly is closed, by pressing the movable handle 3 again, the advancement pawl 31 drives the toothed rack 21 distally, so the toothed rack 21 drives the actuating member 2 to move distally to fire the stapler.

The drive member 46 is rotatably connected to the first linkage member 41 or the second linkage member 42. In the embodiment, as shown in FIGS. 56 and 57, a first mounting groove 414 is provided inside the first linkage member 41, a first end of the drive member 46 enters the first mounting groove 414 and is rotatable around the first end in the first mounting groove 414. When the second end of the drive member 46 is not under external force, the second end of the drive member 46 extends outward from a side surface of the first linkage member 41 facing the connecting rod 18, and the drive member 46 is close to the second side wall 4142 of the first mounting groove 414. In the state of FIG. 56, when the movable handle 3 is pressed to drive the toothed rack 21 to move from the first region to the second region, the toothed rack 21 contacts the second end of the drive member 46 and presses the second end of the drive member 46 downward, the drive member 46 is driven to rotate, so the drive member 46 is moved toward the first side wall 4141 of the first mounting groove 414. At the same time, the elastic member 47 is compressed to deform, and the drive member 46 further enters the first mounting groove 414 and enters the state of FIG. 57, so the drive member 46 no longer blocks the toothed rack 21 from moving. At the same time, the linkage assembly 4 is also maintained in the second state to maintain the stability of the head assembly.

After the stapler is fired, the actuating member 2 is moved proximally by operating the retract member 7, so when the actuating member 2 moves from the second region to the first region, the toothed rack 21 presses the drive member 46 away from the actuating member 2, so the drive member 46 drives the third pivot portion 413 and the fourth pivot portion 423 to move away from the connecting rod 18, and the linkage assembly 4 enters the first state. During this process, the second pivot portion 422 drives the closure drive assembly 5 to move distally, and the closure drive piece 12 is driven to move distally to automatically open the head assembly.

However, in actual disclosures, due to the existence of structural tolerances of dimensional chain or other conditions, the automatic opening structure of the head assembly may fail. For example, the closure drive piece may not return to the specified position when the linkage assembly 4 returns to the first state after firing, so the head assembly is unable to be opened normally, or the opening angle of the head assembly is limited and the head assembly is unable to be opened completely. At this time, the head assembly can be manually opened by operating the reset member 8. In the embodiment, as shown in FIG. 56 and FIG. 58, when the linkage assembly 4 is in the second state, the distal end of the operating portion 81 of the reset member 8 is at a certain distance from the proximal end of the fixing member 14. At the same time, the operating portion 81 of the reset member 8 extends outward from the surface of the housing 13 for easy operation. The operator can press the reset member 8 toward the distal side (i.e., in the direction S7 in FIG. 58) to make the reset member 8 move distally to the position shown in FIG. 59. During this process, under the driving force of the operating portion 81, the reset mating portion 82 drives the second connecting pin 53 to move distally, so the closure drive piece 12 moves distally and opens the head assembly. At the same time, the second connecting pin 53 drives the sleeve portion 51 of the closure drive assembly 5 to move distally, and the drive portion 52 of the closure drive assembly 5 drives the second pivot portion 422 to move distally, so the third pivot portion 413 and the fourth pivot portion 423 move away from the connecting rod 18 to the position shown in FIG. 59, that is, the linkage assembly 4 returns to the first state, and the first return spring 62 and the second return spring 61 also returns to the initial state. Therefore, when the head assembly is closed, the closure drive piece 12 can be driven to retract distally by operating the reset member 8 to manually open the head assembly, so the situation where the closure drive piece 12 fails to return to its initial position and the head assembly cannot be opened normally is avoided.

Figure 60:
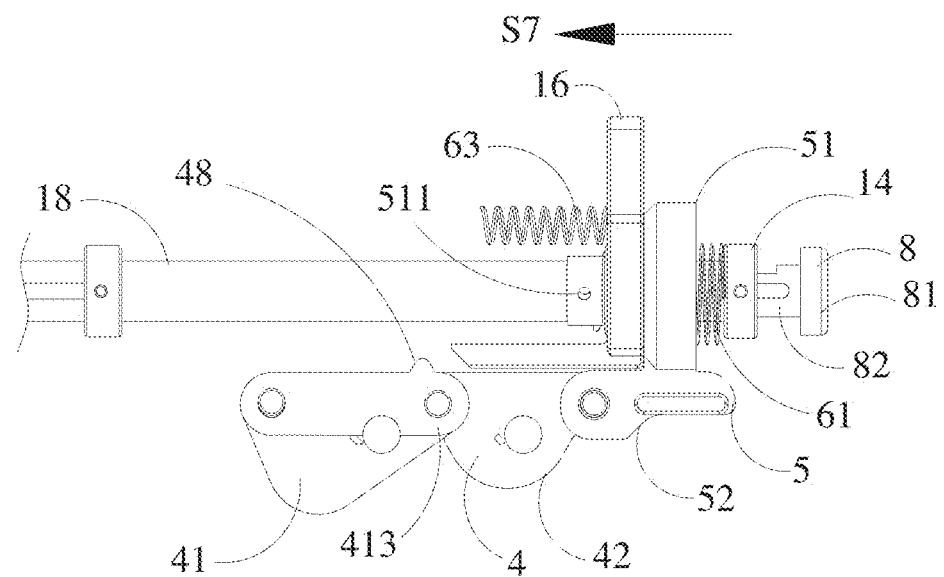
FIG. 60 is a structural schematic view of the closure switch mechanism after the head assembly is closed according to a seventh embodiment of the present disclosure.

FIG. 60 is a structural schematic view of the closure drive mechanism according to the seventh embodiment of the present disclosure. The seventh embodiment is different from the sixth embodiment shown in FIGS. 47 to 59 in that the closure drive mechanism includes a structure for manually closing and manually opening the head assembly. In the embodiment, the closure drive mechanism further includes a switch member 16, one end of the switch member 16 extends outward from the housing of the instrument platform to facilitate the operation. The third pivot portion 413 of the first linkage member 41 is provided with a drive member 48, and the drive member 48 is non-rotatable relative to the first linkage member 41. The switch member 16 is jacketed on the connecting rod 18, and a third return spring 63 is provided between the switch member 16 and the housing of the instrument platform 1. The third return spring 63 may be a compression spring, for example. The switch member 16 is movable between a fifth region and a sixth region, and the fifth region is located at a distal side of the sixth region. In an initial state, the switch member 16 is in the fifth region. The switch member 16 is operated to move proximally, to move from the fifth region to the sixth region. Then the switch member 16 drives the closure drive assembly 5 to move proximally to close the head assembly. At the same time, the closure drive assembly 5 drives the second pivot portion 422 to move proximally through the drive portion 52, and the third pivot portion 413 and the fourth pivot portion 423 of the linkage assembly 4 move toward the connecting rod 18, so the linkage assembly 4 enters the second state from the first state. During the firing process of the stapler, the switch member 16 is located on the proximal side of the drive member 48 and does not act on the linkage assembly 4. The linkage assembly 4 remains in the second state. After the stapler is fired, the switch member 16 is operated to move from the sixth region distally to the fifth region and compress the third return spring 63, and the switch member 16 presses the drive member 48 of the linkage assembly 4 away from the connecting rod 18, so the third pivot portion 413 and the fourth pivot portion 423 move away from the connecting rod 18, and the linkage assembly 4 returns to the first state, then the closure drive assembly 5 moves distally, the closure drive piece 12 is driven by the closure drive assembly 5 to move distally to open the head assembly.

In the seventh embodiment, if the switch member 16 fails or the switch member 16 cannot completely open the head assembly, the operating portion 81 of the reset member 8 can also be pressed in the direction S7 in FIG. 60, so the operating portion 81 drives the reset mating portion 82 to move distally, then the closure drive piece 12 moves toward the distal side to open the head assembly. At the same time, the second connecting pin 53 drives the sleeve portion 51 of the closure drive assembly 5 to move distally, and the drive portion 52 of the closure drive assembly 5 drives the second pivot portion 422 to move distally, so the third pivot portion 413 and the fourth pivot portion 423 move away from the connecting rod 18, and the linkage assembly 4 returns to the first state.

In FIGS. 47 to 59, the closure drive mechanism includes a structure for driving the head assembly to close by the movable handle, a structure for automatically opening the head assembly, and a structure for manually operating the reset member 8 to reset the head assembly when the structure for automatically opening the head assembly fails. In the embodiment of FIG. 60, the closure drive mechanism includes a mechanism for manually closing and opening the head assembly, and a structure for manually operating the reset member 8 to reset the head assembly when the switch member 16 fails. In another alternative embodiment, the reset structure with the reset member in the closure drive mechanism can be cooperated with other structures for opening the stapler, which is different from the structure with the toothed rack and the drive member shown in FIGS. 47 to 59 and the structure with the switch member shown in FIG. 60. In another alternative embodiment, the structure for automatically/manually opening the head assembly may not be provided, but only a structure for driving the head assembly to close by a movable handle and a reset structure with the reset member may be provided. That is, after the head assembly is driven to close by the movable handle, the stapler is driven to fire by the movable handle, and then the head assembly is opened directly by operating the reset member. This also falls within the scope of protection of the present disclosure. In other alternative embodiments, other structures for closing the head assembly may be provided and cooperated with the reset structure with the reset member.

The above is a detailed description of the present disclosure in connection with the specific selective embodiments, and the specific embodiments of the present disclosure are not limited to the description. Modifications and substitutions can be made without departing from the spirit and scope of the present disclosure.

What is claimed is:

1. A closure drive mechanism used for a surgical stapler having an instrument body, comprising:
   a linkage assembly comprising a first pivot portion and a second pivot portion, wherein the first pivot portion is configured to be pivotally connected to the instrument body, and the second pivot portion is configured to be located on a proximal side of the first pivot portion; the linkage assembly has a first state and a second state;
   a movable handle comprising a first mating portion; and
   a closure drive assembly configured to be pivotally connected to the second pivot portion of the linkage assembly;
   wherein, when the linkage assembly is in the first state and the movable handle rotates in a first direction, the first mating portion drives the linkage assembly to enter the second state, the second pivot portion of the linkage assembly moves proximally and drives the closure drive assembly to move proximally.

2. The closure drive mechanism of claim 1, wherein the linkage assembly comprises a first linkage member and a second linkage member on a proximal side of the first linkage member; the first linkage member comprises the first pivot portion and a third pivot portion, the second linkage member comprises the second pivot portion and a fourth pivot portion, and the third pivot portion is configured to be pivotally connected to the fourth pivot portion;
   when the linkage assembly is in the first state and the movable handle rotates in the first direction, the first mating portion drives the first linkage member to rotate in the first direction, the second linkage member rotates in a second direction relative to the first linkage member, and an angle between the first linkage member and the second linkage member increases; the second direction is opposite to the first direction.

3. The closure drive mechanism of claim 2, further comprising a connecting rod, wherein the closure drive assembly is configured to be jacketed on the connecting rod; when the linkage assembly enters the second state from the first state, the third pivot portion and the fourth pivot portion move toward the connecting rod to drive the closure drive assembly to move toward a proximal side of the connecting rod.

4. The closure drive mechanism of claim 3, further comprising a closure drive piece in the connecting rod; wherein the closure drive assembly comprises a sleeve portion and a drive portion configured to be connected to the sleeve portion, the sleeve portion is configured to be jacketed on the connecting rod and connected to a proximal side of the closure drive piece, and the drive portion is configured to pivotally connected to the second pivot portion.

5. The closure drive mechanism of claim 2, wherein the third pivot portion comprises the groove, the fourth pivot portion is at least partially in the groove of the third pivot portion, and the fourth pivot portion is provided with a convex portion; when the linkage assembly is in the second state, the convex portion abuts an outer wall outside the groove to block the second linkage member from rotating in the second direction relative to the first linkage member; or the fourth pivot portion comprises the groove, the third pivot portion is at least partially in the groove of the fourth pivot portion, and the third pivot portion is provided with a convex portion; when the linkage assembly is in the second state, the convex portion abuts the outer wall outside the groove to block the second linkage member from rotating in the second direction relative to the first linkage member.

6. The closure drive mechanism of claim 2, wherein the first linkage member further comprises a second mating portion, and a side surface of the second mating portion facing the movable handle is an arc-shaped surface; when the linkage assembly is in the first state and the movable handle is at an initial position of the movable handle, the second mating portion abuts the first mating portion of the movable handle.

7. The closure drive mechanism of claim 6, wherein the first linkage member is a triangular rod, the first pivot portion and the third pivot portion are respectively provided at a position of a first apex and a position of a second apex of the triangular rod, and the second mating portion is provided at a position of a third apex of the triangular rod; and/or, the second linkage member is a straight rod having a first end provided with the second pivot portion and a second end provided with the fourth pivot portion.

8. The closure drive mechanism of claim 1, further comprising:

a connecting rod configured to extend in an axial direction of the stapler; and a closure drive piece configured to extend in the axial direction of the stapler and at least partially in the connecting rod;

wherein the closure drive assembly comprises:

a first closure member configured to be jacketed on the connecting rod and respectively connected to a proximal side of the connecting rod and a proximal side of the closure drive piece; wherein the connecting rod is configured to drive the closure drive piece and the first closure member to rotate around a central axis of the connecting rod when the connecting rod rotates around the central axis of the connecting rod; and a second closure member configured to be pivotally connected to the second pivot portion of the linkage assembly and at least partially rotatably jacketed on the first closure member; wherein the second closure member is configured to drive the closure drive piece to move proximally through the first closure member when the second closure member moves proximally.

9. The closure drive mechanism of claim 8, wherein the second closure member comprises a sleeve portion jacketed on the first closure member and a drive portion configured to be connected to the sleeve portion, and the first closure member is rotatable around the central axis of the connecting rod relative to the sleeve portion; the drive portion is configured to be pivotally connected to the second pivot portion of the linkage assembly;

the first closure member comprises a shaft portion and a disc portion on a proximal side of the shaft portion; a proximal side of the sleeve portion of the second closure member is provided with an annular first stepped surface, the shaft portion is at least partially in the sleeve portion, and the disc portion is on a proximal side of the first stepped surface; an outer diameter of the shaft portion is smaller than an inner diameter of the first stepped surface, and the inner diameter of the first stepped surface is smaller than an outer diameter of the disc portion.

10. The closure drive mechanism of claim 2, further comprising:

an actuating member comprising a switch member, wherein the actuating member is movable between a first region and a second region, the second region is at a distal side of the first region; and a closure drive piece having a proximal side configured to be fixedly connected to the closure drive assembly;

wherein, when the linkage assembly is in the second state and the actuating member moves from the second region to the first region, the switch member forces the linkage assembly away from the actuating member, so the linkage assembly enters the first state, the third pivot portion and the fourth pivot portion move away from the actuating member, and the second pivot portion drives the closure drive piece to move distally through the closure drive assembly.

11. The closure drive mechanism of claim 10, wherein the linkage assembly further comprises a drive member configured to be mounted on the first linkage member or the second linkage member; a first end of the drive member is convex from a side surface of the first linkage member or the second linkage member facing the actuating member;

when the linkage assembly is in the second state and the actuating member moves from the second region to the first region, the switch member forces the first end of the drive member away from the actuating member.

12. The closure drive mechanism of claim 11, wherein, when the linkage assembly is in the second state and the actuating member moves from the first region to the second region, the first linkage member remains stationary relative to the second linkage member, the switch member drives the first end of the drive member to move distally, so the drive member doesn't block the actuating member from moving;

when the linkage assembly is in the second state and the actuating member moves from the second region to the first region, the first linkage member is rotated relative to the second linkage member.

13. The closure drive mechanism of claim 12, wherein a mounting groove is provided on a surface of the first linkage member or the second linkage member facing the actuating member, and the drive member is in the mounting groove;

the mounting groove comprises a first side wall, a second side wall and a bottom wall, the first side wall of the mounting groove is on a distal side of the second side wall, and a first gap is formed between the drive member and the first side wall of the mounting groove; when the linkage assembly is in the first state, the drive member abuts the second side wall of the mounting groove; when the linkage assembly is in the second state and the actuating member moves from the first region to the second region, the drive member moves toward the first side wall of the mounting groove.

14. The closure drive mechanism of claim 12, wherein at least one side of the first linkage member is provided with the drive member, the drive member is configured to be rotatably connected to a side wall of the first linkage member, and the switch member is a drive tooth on at least one side of the actuating member;

the first linkage member is further provided with a block portion on a proximal side of the drive member, and the block portion blocks a second end of the drive member from moving proximally.

15. The closure drive mechanism of claim 2, further comprising:

a connecting rod configured to extend in an axial direction of the stapler;

a closure drive piece at least partially in the connecting rod and movable in the axial direction relative to the connecting rod, wherein a first stop portion is configured to be fixedly located on a proximal side of the closure drive piece; and a reset member on a proximal side of the connecting rod, wherein the reset member is at least partially in the connecting rod and movable in the axial direction relative to the connecting rod; the reset member is configured to drive the closure drive piece to move distally when the reset member is driven to move distally.

16. The closure drive mechanism of claim 15, wherein the closure drive mechanism further comprises a second stop portion configured to be located on a proximal side of the first stop portion and fixed in the axial direction to a housing of the instrument body;

the reset member is configured to abut the first stop portion when the reset member is driven to move distally, and the reset member is configured to be stopped at the second stop portion when the reset member is driven to move proximally;

the instrument body is provided with a mating portion for the second stop portion, and the second stop portion is configured to be rotatably connected with the mating portion.

17. The closure drive mechanism of claim 16, wherein the mating portion for the second stop portion is a circumferential groove on the housing, the second stop portion is a first connecting pin configured to be movably located on the reset member, and the first connecting pin is configured to be rotatably located in the circumferential groove.

18. The closure drive mechanism of claim 17, further comprising an annular fixing member, wherein the first connecting pin is configured to be fixedly connected to the fixing member, and the fixing member is rotatably in the circumferential groove;

the reset member is at least partially in the fixing member, and the reset member is movable in the axial direction relative to the fixing member.

19. The closure drive mechanism of claim 17, wherein the reset member comprises a reset mating portion and an operating portion configured to be located on a proximal side of the reset mating portion, the operating portion is on a proximal side of the second stop portion, the second stop portion is configured to pass through the reset mating portion, and the reset mating portion is movable in the axial direction relative to the second stop portion.

20. A surgical stapler comprising the closure drive mechanism according to claim 1.

* * * * *